United States Patent [19]
Aversa et al.

[11] Patent Number: 5,977,303
[45] Date of Patent: Nov. 2, 1999

[54] MAMMALIAN CELL SURFACE ANTIGENS

[75] Inventors: Gregorio Aversa, Palo Alto; Chia-Chun J. Chang, San Jose; Benjamin G. Cocks, Mountain View; Jan E. de Vries, Los Altos, all of Calif.

[73] Assignee: Schering Corporation, Kenilworth, N.J.

[21] Appl. No.: 08/462,738

[22] Filed: Jun. 5, 1995

Related U.S. Application Data

[62] Division of application No. 08/348,792, Dec. 2, 1994, abandoned.

[51] Int. Cl.$^6$ .................................................. C07K 14/00
[52] U.S. Cl. ..................... 530/350; 530/300; 435/69.6; 435/69.7; 514/12
[58] Field of Search ................................. 530/300, 350, 530/387.1; 435/69.6, 69.7; 514/12

[56] References Cited

U.S. PATENT DOCUMENTS 5,274,087  12/1993  Barnett et al. ........................ 536/23.5

FOREIGN PATENT DOCUMENTS

| WO 92/00092 | 1/1992 | WIPO . |
|---|---|---|
| WO 63/004311 | 1/1993 | WIPO . |
| WO 93/19782 | 10/1993 | WIPO . |

OTHER PUBLICATIONS

Miyuki Azuma, et al. "Functional Expression of B7/BB1 on Activated T Lymphocytes," *J. Exp. Med.,* 177:845–850, Mar. 1993.
Miyuki Azuma, et al. "B70 Anitgen is a Second Ligand for CTLA–4 and CD28," *Nature* 366:76–79, Nov. 1993.
Barbara E. Bierer, et al., "T Cell Adhesion, Avidity Regulation and Signalinmg: A Molecular Analysis of CD2," *Semin. Immunol.* 5:249–261, 1993.
Marie T. Filbin, et al., "Role of Myelin Po Protein as a Homophilic Adhesion Molecule," *Nature* 344:871–872, Apr. 1990.
Gordon J. Freeman, et al., "Cloning of B7-2: A CTLA Counter–Receptor that Costimualtes Human T Cell Proliferation," *Science* 262:909–911, Nov. 1993.
Jonathan M. Green, et al., "Absence of B7–Dependent Responses in CD28–Deficient Mice," *Immunity* 1:501–508, Sep. 1994.
Martin Grumet, et al., "Neuron–Glia Cell Adhesion Molecule Interacts with Neurons and Astroglia via Different Binding Mechanisms," *J. Cell Biol.* 106:487–503, Feb. 1988.
Marc K. Jenkins, et al., "Molecules Involved in T–Cell Costimulation," *Curr. Opin. Immunol.* 5:361–367, 1993.
Marc K. Jenkins, "The Ups and Downs of T Cell Costimulation," *Immunity* 1:443–446, Sep. 1994.
Carl H. June, et al., "Role of the CD28 Receptor in T–Cell Activation," *Immunol. Today* 11:211–216, 1990.

Peter S. Linsley, et al "T–Cell Antigen CD28 Mediates Adhesion with B Cells by Interacting with Activiation Antigen B7/BB1," *Proc. Natl. Acad Sci.* 87:5031–5035, Jul. 1990.
Porunellor A. Mathew, et al., "Cloning and Characterization of the 2B4 Gene Encoding a Molecule Associated with Non–MHC–Restricted Killing Mediated by Activated Natural Killer Cells and T Cells," *J. Immunol.* 151:5328–5337, Nov. 1993.
Kiyoshi Matsui, et al., "Low Affinity Interaction of Peptide–MHC Complexes with T Cell Receptors," *Science,* 254:1788–1791, Dec. 1991.
Vincent P. Mauro, et al., "Homophilic and Heterophilic Binding Activities of Nr–CAM, a Nervous System Cell Adhesion Molecule," *J. Cell Biol.* 119:191–202, Oct. 1992.
Geraldo M.B. Pereira, et al., "Mechanism of Action of Cyclosporin A in Vivo: II. T Cell Priming in Vivo to Alloantigen Can Be Mediated by an IL–2–Independent Cyclosporine A–Resistant Pathway," *J. Immunol.* 144:2109–2116, Mar. 1990.
Danielle Pham–Dinh, et al., "The Major Peripheral Myelin Protein Zero Gene: Structure and Localization in the Cluster of Fcγ Receptor Genes on Human Chromosome 1q21.3–q23," *Human Molec. Genet.* 2:2051–2054, 1993.
Yong Rao, et al., "Identification of a Peptide Sequence Involved in Homophilic Binding in the Neural Cell Adhesion Molecule NCAM," *J. Cell Biol.* 118:937–949, Aug. 1992.
Franca Ronchese, et al., "Mice Transgenic for a Soluble Form of Murine CTLA–4 Show Enhanced Expansion of Antigen–Specific CD4+ T Cell and Defective Anibody Production In Vivo," *J. Exp. Med.* 179:809–817, Mar. 1994.
Brian Seed, "An LFA–3 cDNA Encodes a Phosphlipid–Linked Membrane Protein Homologous to Its Receptor CD2," *Nature* 329:840–842, Oct. 1992.
Periasamy Selvaraj, et al., "The T Lymphocyte Glycoprotein CD2 Binds The Cell Surface Ligand LFA–3," *Nature* 326:400–403, Mar. 1987.
Arda Shahinian, et al., Differential T Cell Costimulatory Requirements in CD28–Deficient Mice, *Science* 261:609–612, Jul. 1993.
Zhou Songyang, et al., "SH2 Domains Recognize Specific Phosphopeptide Sequences," *Cell* 72:767–778, Mar. 1993.
Donald E. Staunton, et al., "Molecular Cloning of the Lymphocyte Activation Marker Blast–1," *EMBO J.* 6:3695–3701, 1987.

(List continued on next page.)

*Primary Examiner*—Sheela Huff
*Assistant Examiner*—Julie E Reeves
*Attorney, Agent, or Firm*—Sheela Mohan-Peterson; Gerald P. Keleher; Edwin P. Ching

[57] ABSTRACT

Purified genes encoding a T cell surface antigen from a mammal, reagents related thereto including purified proteins, specific antibodies, and nucleic acids encoding said antigen. Methods of using said reagents and diagnostic kits are also provided.

30 Claims, No Drawings

OTHER PUBLICATIONS

Donald E. Staunton, et al., "Blast–1 Possesses a Glycoyl–Phosphatidylinositol (GPI) Membrane Anchor, Is Related to LFA–3 and OX–45 and Maps to Chromosome 1q21–23," *J. Exp. Med.* 169:1087–1099, Mar. 1989.

P. Anton van der Merwe, et al., "Affinity and Kinetic Analysis of the Interaction of the Cell Adhesion Molecules Rat CD2 and CD48," *EMBO J.* 12:4045–4954, 1993.

Mark L. Watson, et al., "Genomic Organization of the Selectin Family of Leukocyte Adhesion Moleucles on Human and Mouse Chromosome 1," *J. Exp. Med.* 172:263–272, Jul. 1990.

Suzanne M. Watt, et al., "The Heparin Binding PECAM–1 Adhesion Molecule Is Expressed by CD34+ Hematopoietic Precursor Cells with Early Myeloid and B–Lymphoid Cell Phenotypes," *Blood* 9:2649–2663, Nov. 1993.

Alan F. Williams, et al., "The Immunoglobulin Superfamily–Domains for Cell Surface Recognition," *Ann. Rev. Immunol.* 6:381–405, 1988.

A. Zeevi, et al., "Sensitivity of Activated Human Lymphocytes to Cyclosporin and Its Metabolites," *Hum. Immunol.* 21:142–153, 1988.

Hau Zhou, et al., "Homophilic Adhesion between Ig Superfamily Carcinoembyonic Antigen Molecules Involves Double Reciprocal Bonds," *J. Cell Biol.* 122:951–960, Aug. 1993.

Benjamin G. Cocks, et al., *Nature,* 376:260–263, Jul. 20, 1995. "A novel receptor involved in T–cell activation".

Jan E. de Vries, et al., *Journal of Cellular Biochemistry,* Supplement 21A, p. 67, Astract No. C2–118, 1995. Keystone Symposium on Control and Manipulation of the Immune System, Taos, New Mexico, USA, Mar. 16–22, 1995. "SLAM: A Novel Co–Stimulatory Molecule for Human T Cells".

Nigel Kileen, et al., *EMBO Journal,* 7(10):3087–3091, 1988. "The MRC OX–45 antigen of rat leukocytes and endothelium is in a subset of the immunoglobulin superfamily with CD2, LFA–3 and carcinoembryonic antigens".

Vladimir Korinek, et al., *Immunogenetics,* 33:108–112, 1991. "The human leucocyte antigen CD48 (MEM–102) is closely related to the activation marker Blast–1".

Dominique Schols, et al., *Journal of Cellular Biochemistry,* Supplement 21A, p. 83, Astract No. C2–181, 1995. Keystone Symposium on Control and Manipulation of the Immune System, Taos, New Mexico, USA, Mar. 16–22, 1995. "A Role for SLAM, A Novel T Cell Costimulatory Molecule, in Regulating Human Thymocyte Development".

A. Swaroop, et al., *EMBL Sequence Database Release 32,* Accession No. M91394, Jul. 21, 1992. "Human mRNA sequence' sequence identity >97% in 184bp overlap to reverse complement of sequence ID No. 3 from pos. 1849".

Killeen et al EMBO Journal vol. 7 No. 10 3087–3091, 1988.

Sandrin et al J Immunology vol. 149 No. 5 1636–1641, Sep. 1992.

Ponger et al Methods in Enzymology vol. 154 450–473, 1987.

Creighton Prog Biophys Molec Biol vol. 33 231–297, 1975.

Creighton Proteins: Structure and Molceular Principles WH Freeman and Co NY 93–94, 1983.

Burgess et al Journal of Cell biology vol. 111 2129–2138, Nov. 1990.

Lazar et al Molecular and Cellular Biology vol. 8 No. 3 1247–1252, Mar. 1988.

Schwarz et al Proc Natl Acad Sci USA vol. 84 6408–6411, Sep. 1987.

Lin et al Biochemistry vol. 14 No. 8 1559–1563, 1975.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1716 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 61..1065

(xi) SEQUENCE DESCRIPTION: SEQ ID NO:1:

```
AGGCATCTGT GAGCAGCTGC CAGGCTCCGG CCAGGATCCC TTCCTTCTCC TCATTGGCTG        60

ATG GAT CCC AAG GGG CTC CTC TCC TTG ACC TTC GTG CTG TTT CTC TCC        108
Met Asp Pro Lys Gly Leu Leu Ser Leu Thr Phe Val Leu Phe Leu Ser
  1               5                  10                  15

CTG GCT TTT GGG GCA AGC TAC GGA ACA GGT GGG CGC ATG ATG AAC TGC        156
Leu Ala Phe Gly Ala Ser Tyr Gly Thr Gly Gly Arg Met Met Asn Cys
             20                  25                  30

CCA AAG ATT CTC CGG CAG TTG GGA AGC AAA GTG CTG CTG CCC CTG ACA        204
Pro Lys Ile Leu Arg Gln Leu Gly Ser Lys Val Leu Leu Pro Leu Thr
         35                  40                  45

TAT GAA AGG ATA AAT AAG AGC ATG AAC AAA AGC ATC CAC ATT GTC GTC        252
Tyr Glu Arg Ile Asn Lys Ser Met Asn Lys Ser Ile His Ile Val Val
     50                  55                  60

ACA ATG GCA AAA TCA CTG GAG AAC AGT GTC GAG AAC AAA ATA GTG TCT        300
Thr Met Ala Lys Ser Leu Glu Asn Ser Val Glu Asn Lys Ile Val Ser
 65                  70                  75                  80
```

```
CTT GAT CCA TCC GAA GCA GGC CCT CCA CGT TAT CTA GGA GAT CGC TAC     348
Leu Asp Pro Ser Glu Ala Gly Pro Pro Arg Tyr Leu Gly Asp Arg Tyr
                 85                  90                  95

AAG TTT TAT CTG GAG AAT CTC ACC CTG GGG ATA CGG GAA AGC AGG AAG     396
Lys Phe Tyr Leu Glu Asn Leu Thr Leu Gly Ile Arg Glu Ser Arg Lys
                100                 105                 110

GAG GAT GAG GGA TGG TAC CTT ATG ACC CTG GAG AAA AAT GTT TCA GTT     444
Glu Asp Glu Gly Trp Tyr Leu Met Thr Leu Glu Lys Asn Val Ser Val
                115                 120                 125

CAG CGC TTT TGC CTG CAG TTG AGG CTT TAT GAG CAG GTC TCC ACT CCA     492
Gln Arg Phe Cys Leu Gln Leu Arg Leu Tyr Glu Gln Val Ser Thr Pro
            130                 135                 140

GAA ATT AAA GTT TTA AAC AAG ACC CAG GAG AAC GGG ACC TGC ACC TTG     540
Glu Ile Lys Val Leu Asn Lys Thr Gln Glu Asn Gly Thr Cys Thr Leu
145                 150                 155                 160

ATA CTG GGC TGC ACA GTG GAG AAG GGG GAC CAT GTG GCT TAC AGC TGG     588
Ile Leu Gly Cys Thr Val Glu Lys Gly Asp His Val Ala Tyr Ser Trp
                165                 170                 175

AGT GAA AAG GCG GGC ACC CAC CCA CTG AAC CCA GCC AAC AGC TCC CAC     636
Ser Glu Lys Ala Gly Thr His Pro Leu Asn Pro Ala Asn Ser Ser His
                180                 185                 190

CTC CTG TCC CTC ACC CTC GGC CCC CAG CAT GCT GAC AAT ATC TAC ATC     684
Leu Leu Ser Leu Thr Leu Gly Pro Gln His Ala Asp Asn Ile Tyr Ile
            195                 200                 205

TGC ACC GTG AGC AAC CCT ATC AGC AAC AAT TCC CAG ACC TTC AGC CCG     732
Cys Thr Val Ser Asn Pro Ile Ser Asn Asn Ser Gln Thr Phe Ser Pro
    210                 215                 220

TGG CCC GGA TGC AGG ACA GAC CCC TCA GAA ACA AAA CCA TGG GCA GTG     780
Trp Pro Gly Cys Arg Thr Asp Pro Ser Glu Thr Lys Pro Trp Ala Val
225                 230                 235                 240

TAT GCT GGG CTG TTA GGG GGT GTC ATC ATG ATT CTC ATC ATG GTG GTA     828
Tyr Ala Gly Leu Leu Gly Gly Val Ile Met Ile Leu Ile Met Val Val
                245                 250                 255

ATA CTA CAG TTG AGA AGA AGA GGT AAA ACG AAC CAT TAC CAG ACA ACA     876
Ile Leu Gln Leu Arg Arg Arg Gly Lys Thr Asn His Tyr Gln Thr Thr
            260                 265                 270

GTG GAA AAA AAA AGC CTT ACG ATC TAT GCC CAA GTC CAG AAA CCA GGT     924
Val Glu Lys Lys Ser Leu Thr Ile Tyr Ala Gln Val Gln Lys Pro Gly
275                 280                 285

CCT CTT CAG AAG AAA CTT GAC TCC TTC CCA GCT CAG GAC CCT TGC ACC     972
Pro Leu Gln Lys Lys Leu Asp Ser Phe Pro Ala Gln Asp Pro Cys Thr
        290                 295                 300

ACC ATA TAT GTT GCT GCC ACA GAG CCT GTC CCA GAG TCT GTC CAG GAA    1020
Thr Ile Tyr Val Ala Ala Thr Glu Pro Val Pro Glu Ser Val Gln Glu
305                 310                 315                 320

ACA AAT TCC ATC ACA GTC TAT GCT AGT GTG ACA CTT CCA GAG AGC        1065
Thr Asn Ser Ile Thr Val Tyr Ala Ser Val Thr Leu Pro Glu Ser
                325                 330                 335

TGACACCAGA GACCAACAAA GGGACTTTCT GAAGGAAAAT GGAAAAACCA AAATGAACAC  1125

TGAACTTGGC CACAGGCCCA AGTTTCCTCT GGCAGACATG CTGCACGTCT GTACCCTTCT  1185

CAGATCAACT CCCTGGTGAT GTTTCTTCCA CATACATCTG TGAAATGAAC AAGGAAGTGA  1245

GGCTTCCCAA GAATTTAGCT TGCTGTGCAG TGGCTGCAGG CGCAGAACAG AGCGTTACTT  1305

GATAACAGCG TTCCATCTTT GTGTTGTAGC AGATGAAATG GACAGTAATG TGAGTTCAGA  1365

CTTTGGGCAT CTTGCTCTTG GCTGGAACTG ATAATAAAAA TCAGACTGAA AGCCAGGACA  1425

TCTGAGTACC TATCTCACAC ACTGACCACC AGTCACAAAG TCTGGAAAAG TTTACATTTT  1485

GGCTATCTTT ACTTTGTTCT GGGAGCTGAT CATGATAACC TGCAGACCTG ATCAAGCCTC  1545
```

```
TGTGCCTCAG TTTCTCTCTC AGGATAAAGA GTGAATAGAG GCCGAAGGGT GAATTTCTTA    1605

TTATACATAA AACACTCTGA TATTATTGTA TAAAGGAAGC TAAGAATATT ATTTTATTTG    1665

CAAAACCCAG AAGCTAAAAA GTCAATAAAC AGAAAGAATG ATTTTGAGAA A             1716
```

(2) INFORMATION FOR SEQ ID NO:2:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Pro Lys Gly Leu Leu Ser Leu Thr Phe Val Leu Phe Leu Ser
 1               5                  10                  15

Leu Ala Phe Gly Ala Ser Tyr Gly Thr Gly Gly Arg Met Met Asn Cys
                20                  25                  30

Pro Lys Ile Leu Arg Gln Leu Gly Ser Lys Val Leu Pro Leu Thr
                35                  40                  45

Tyr Glu Arg Ile Asn Lys Ser Met Asn Lys Ser Ile His Ile Val Val
        50                  55                  60

Thr Met Ala Lys Ser Leu Glu Asn Ser Val Glu Asn Lys Ile Val Ser
65                  70                  75                  80

Leu Asp Pro Ser Glu Ala Gly Pro Pro Arg Tyr Leu Gly Asp Arg Tyr
                85                  90                  95

Lys Phe Tyr Leu Glu Asn Leu Thr Leu Gly Ile Arg Glu Ser Arg Lys
                100                 105                 110

Glu Asp Glu Gly Trp Tyr Leu Met Thr Leu Glu Lys Asn Val Ser Val
                115                 120                 125

Gln Arg Phe Cys Leu Gln Leu Arg Leu Tyr Glu Gln Val Ser Thr Pro
        130                 135                 140

Glu Ile Lys Val Leu Asn Lys Thr Gln Glu Asn Gly Thr Cys Thr Leu
145                 150                 155                 160

Ile Leu Gly Cys Thr Val Glu Lys Gly Asp His Val Ala Tyr Ser Trp
                165                 170                 175

Ser Glu Lys Ala Gly Thr His Pro Leu Asn Pro Ala Asn Ser Ser His
                180                 185                 190

Leu Leu Ser Leu Thr Leu Gly Pro Gln His Ala Asp Asn Ile Tyr Ile
        195                 200                 205

Cys Thr Val Ser Asn Pro Ile Ser Asn Asn Ser Gln Thr Phe Ser Pro
210                 215                 220

Trp Pro Gly Cys Arg Thr Asp Pro Ser Glu Thr Lys Pro Trp Ala Val
225                 230                 235                 240

Tyr Ala Gly Leu Leu Gly Gly Val Ile Met Ile Leu Ile Met Val Val
                245                 250                 255

Ile Leu Gln Leu Arg Arg Arg Gly Lys Thr Asn His Tyr Gln Thr Thr
                260                 265                 270

Val Glu Lys Lys Ser Leu Thr Ile Tyr Ala Gln Val Gln Lys Pro Gly
        275                 280                 285

Pro Leu Gln Lys Lys Leu Asp Ser Phe Pro Ala Gln Asp Pro Cys Thr
        290                 295                 300

Thr Ile Tyr Val Ala Ala Thr Glu Pro Val Pro Glu Ser Val Gln Glu
305                 310                 315                 320

Thr Asn Ser Ile Thr Val Tyr Ala Ser Val Thr Leu Pro Glu Ser
```

325              330              335

(2) INFORMATION FOR SEQ ID NO:3:

(i) SEQUENCE CHARACTERISTICS:
        (A) LENGTH: 1852 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 61..954

(xi) SEQUENCE DESCRIPTION: SEQ ID NO:3:

```
TGGCATCTGT GAGCAGCTGC CAGGCTCCGG CCAGGATCCC TTCCTTCTCC TCATTGGCTG      60

ATG GAT CCC AAG GGG CTC CTC TCC TTG ACC TTC GTG CTG TTT CTC TCC       108
Met Asp Pro Lys Gly Leu Leu Ser Leu Thr Phe Val Leu Phe Leu Ser
 1               5                  10                  15

CTG GCT TTT GGG GCA AGC TAC GGA ACA GGT GGG CGC ATG ATG AAC TGC       156
Leu Ala Phe Gly Ala Ser Tyr Gly Thr Gly Gly Arg Met Met Asn Cys
             20                  25                  30

CCA AAG ATT CTC CGG CAG TTG GGA AGC AAA GTG CTG CTG CCC CTG ACA       204
Pro Lys Ile Leu Arg Gln Leu Gly Ser Lys Val Leu Leu Pro Leu Thr
         35                  40                  45

TAT GAA AGG ATA AAT AAG AGC ATG AAC AAA AGC ATC CAC ATT GTC GTC       252
Tyr Glu Arg Ile Asn Lys Ser Met Asn Lys Ser Ile His Ile Val Val
     50                  55                  60

ACA ATG GCA AAA TCA CTG GAG AAC AGT GTC GAG AAC AAA ATA GTG TCT       300
Thr Met Ala Lys Ser Leu Glu Asn Ser Val Glu Asn Lys Ile Val Ser
 65                  70                  75                  80

CTT GAT CCA TCC GAA GCA GGC CCT CCA CGT TAT CTA GGA GAT CGC TAC       348
Leu Asp Pro Ser Glu Ala Gly Pro Pro Arg Tyr Leu Gly Asp Arg Tyr
                 85                  90                  95

AAG TTT TAT CTG GAG AAT CTC ACC CTG GGG ATA CGG GAA AGC AGG AAG       396
Lys Phe Tyr Leu Glu Asn Leu Thr Leu Gly Ile Arg Glu Ser Arg Lys
            100                 105                 110

GAG GAT GAG GGA TGG TAC CTT ATG ACC CTG GAG AAA AAT GTT TCA GTT       444
Glu Asp Glu Gly Trp Tyr Leu Met Thr Leu Glu Lys Asn Val Ser Val
        115                 120                 125

CAG CGC TTT TGC CTG CAG TTG AGG CTT TAT GAG CAG GTC TCC ACT CCA       492
Gln Arg Phe Cys Leu Gln Leu Arg Leu Tyr Glu Gln Val Ser Thr Pro
    130                 135                 140

GAA ATT AAA GTT TTA AAC AAG ACC CAG GAG AAC GGG ACC TGC ACC TTG       540
Glu Ile Lys Val Leu Asn Lys Thr Gln Glu Asn Gly Thr Cys Thr Leu
145                 150                 155                 160

ATA CTG GGC TGC ACA GTG GAG AAG GGG GAC CAT GTG GCT TAC AGC TGG       588
Ile Leu Gly Cys Thr Val Glu Lys Gly Asp His Val Ala Tyr Ser Trp
                165                 170                 175

AGT GAA AAG GCG GGC ACC CAC CCA CTG AAC CCA GCC AAC AGC TCC CAC       636
Ser Glu Lys Ala Gly Thr His Pro Leu Asn Pro Ala Asn Ser Ser His
            180                 185                 190

CTC CTG TCC CTC ACC CTC GGC CCC CAG CAT GCT GAC AAT ATC TAC ATC       684
Leu Leu Ser Leu Thr Leu Gly Pro Gln His Ala Asp Asn Ile Tyr Ile
        195                 200                 205

TGC ACC GTG AGC AAC CCT ATC AGC AAC AAT TCC CAG ACC TTC AGC CCG       732
Cys Thr Val Ser Asn Pro Ile Ser Asn Asn Ser Gln Thr Phe Ser Pro
    210                 215                 220

TGG CCC GGA TGC AGG ACA GAC CCC TCA GAA ACA AAA CCA TGG GCA GTG       780
Trp Pro Gly Cys Arg Thr Asp Pro Ser Glu Thr Lys Pro Trp Ala Val
225                 230                 235                 240
```

-continued

```
TAT GCT GGG CTG TTA GGG GGT GTC ATC ATG ATT CTC ATC ATG GTG GTA      828
Tyr Ala Gly Leu Leu Gly Gly Val Ile Met Ile Leu Ile Met Val Val
                245                 250                 255

ATA CTA CAG TTG AGA AGA AGA GGT AAA ACG AAC CAT TAC CAG ACA ACA      876
Ile Leu Gln Leu Arg Arg Arg Gly Lys Thr Asn His Tyr Gln Thr Thr
                260                 265                 270

GTG GAA AAA AAA AGC CTT ACG ATC TAT GCC CAA GTC CAG AAA CCA GGT      924
Val Glu Lys Lys Ser Leu Thr Ile Tyr Ala Gln Val Gln Lys Pro Gly
            275                 280                 285

GAC ACT CAT CAT CAG ACT TCG GAC TTA TTC TAATCCAGGA TGACCTTATT        974
Asp Thr His His Gln Thr Ser Asp Leu Phe
            290                 295

TTGAAATCCT TATCTTGACA TCTGTGAAGA CCTTTATTCA AATAAAGTCA CATTTTGACA   1034

TTCTGCGAGG GGCTGGAGCC GGGCCGGGGC GATGTGGAGC GCGGGCCGCG GCGGGGCTGC   1094

CTGGCCGGTG CTGTTGGGGC TGCTGCTGGC GCTGTTAGTG CCGGGCGGTG GTGCCGCCAA   1154

GACCGGTGCG GAGCTCGTGA CTGCGGGTCG GTGCTGAAGC TGCTCAATAC GCACCACCGG   1214

TGCGGCTGCA CTCGCACGAC ATCAAATACG GATCCGGCAG CGGCCAGCAA TCGGTGACCG   1274

GCGTAGAGGT CGGAGCGACG AATAGCTACT GGCGGATCCG CGGCGGCTCG GAGGGGGGTG   1334

CCCGCGCGGG TCCCCGGTGC GCTGCGGGCA GGCGGTGAGG TCACACATGT GCTTACGGGC   1394

AAGAACCTGC ACACGCACCA CTTCCCGTCG CCGCTGTCCA ACAACCAGGA AGTGAGTGCC   1454

AAAGGGGAAG ACGGCGAGGG CGACGACCTG GACCTATGGA CAGTGCGCTG CTCTGCTCTG   1514

GACAGCACTG GGAGCGTGAG GCTGCTGTGG CGCCTTCCAG CATGTGGCAC CTCTGTGGTT   1574

CCTGTCAGTC ACGGTAGCAG TATGGAAGCC CCATCCGTGG GCAGCATGAG GTCCACGCAT   1634

GCCCAGTGCC AACACGCACA ATACGTGGAA GGCCATGGAA GGCATCTTCA TCAAGCCTAG   1694

TGTGGAGCCC TCTGCAGGTC ACGATGAACT CTGAGTGTGT GGATGGATGG GTGGATGGAG   1754

GGTGGCAGGT GGGGCGTCTG CAGGGCCACT CTTGGCAGAG ACTTTGGGTT TGTAGGGGTC   1814

CTCAAGTGCC TTTGTGATTA AAGAATGTTG GTCTATGA                           1852
```

(2) INFORMATION FOR SEQ ID NO:4:

(i) SEQUENCE CHARACTERISTICS:
        (A) LENGTH: 298 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Pro Lys Gly Leu Leu Ser Leu Thr Phe Val Leu Phe Leu Ser
  1               5                  10                  15

Leu Ala Phe Gly Ala Ser Tyr Gly Thr Gly Gly Arg Met Met Asn Cys
                20                  25                  30

Pro Lys Ile Leu Arg Gln Leu Gly Ser Lys Val Leu Leu Pro Leu Thr
            35                  40                  45

Tyr Glu Arg Ile Asn Lys Ser Met Asn Lys Ser Ile His Ile Val Val
        50                  55                  60

Thr Met Ala Lys Ser Leu Glu Asn Ser Val Glu Asn Lys Ile Val Ser
 65                  70                  75                  80

Leu Asp Pro Ser Glu Ala Gly Pro Pro Arg Tyr Leu Gly Asp Arg Tyr
                85                  90                  95

Lys Phe Tyr Leu Glu Asn Leu Thr Leu Gly Ile Arg Glu Ser Arg Lys
            100                 105                 110
```

Glu Asp Glu Gly Trp Tyr Leu Met Thr Leu Glu Lys Asn Val Ser Val
         115                 120                 125

Gln Arg Phe Cys Leu Gln Leu Arg Leu Tyr Glu Gln Val Ser Thr Pro
     130                 135                 140

Glu Ile Lys Val Leu Asn Lys Thr Gln Glu Asn Gly Thr Cys Thr Leu
145                 150                 155                 160

Ile Leu Gly Cys Thr Val Glu Lys Gly Asp His Val Ala Tyr Ser Trp
                 165                 170                 175

Ser Glu Lys Ala Gly Thr His Pro Leu Asn Pro Ala Asn Ser Ser His
             180                 185                 190

Leu Leu Ser Leu Thr Leu Gly Pro Gln His Ala Asp Asn Ile Tyr Ile
         195                 200                 205

Cys Thr Val Ser Asn Pro Ile Ser Asn Asn Ser Gln Thr Phe Ser Pro
    210                 215                 220

Trp Pro Gly Cys Arg Thr Asp Pro Ser Glu Thr Lys Pro Trp Ala Val
225                 230                 235                 240

Tyr Ala Gly Leu Leu Gly Gly Val Ile Met Ile Leu Ile Met Val Val
                245                 250                 255

Ile Leu Gln Leu Arg Arg Arg Gly Lys Thr Asn His Tyr Gln Thr Thr
             260                 265                 270

Val Glu Lys Lys Ser Leu Thr Ile Tyr Ala Gln Val Gln Lys Pro Gly
        275                 280                 285

Asp Thr His His Gln Thr Ser Asp Leu Phe
        290                 295

(2) INFORMATION FOR SEQ ID NO:5:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 61..975

(xi) SEQUENCE DESCRIPTION: SEQ ID NO:5:

AGGCATCTGT GAGCAGCTGC CAGGCTCCGG CCAGGATCCC TTCCTTCTCC TCATTGGCTG     60

ATG GAT CCC AAG GGG CTC CTC TCC TTG ACC TTC GTG CTG TTT CTC TCC     108
Met Asp Pro Lys Gly Leu Leu Ser Leu Thr Phe Val Leu Phe Leu Ser
 1               5                  10                  15

CTG GCT TTT GGG GCA AGC TAC GGA ACA GGT GGG CGC ATG ATG AAC TGC     156
Leu Ala Phe Gly Ala Ser Tyr Gly Thr Gly Gly Arg Met Met Asn Cys
             20                  25                  30

CCA AAG ATT CTC CGG CAG TTG GGA AGC AAA GTG CTG CTG CCC CTG ACA     204
Pro Lys Ile Leu Arg Gln Leu Gly Ser Lys Val Leu Leu Pro Leu Thr
         35                  40                  45

TAT GAA AGG ATA AAT AAG AGC ATG AAC AAA AGC ATC CAC ATT GTC GTC     252
Tyr Glu Arg Ile Asn Lys Ser Met Asn Lys Ser Ile His Ile Val Val
     50                  55                  60

ACA ATG GCA AAA TCA CTG GAG AAC AGT GTC GAG AAC AAA ATA GTG TCT     300
Thr Met Ala Lys Ser Leu Glu Asn Ser Val Glu Asn Lys Ile Val Ser
 65                  70                  75                  80

CTT GAT CCA TCC GAA GCA GGC CCT CCA CGT TAT CTA GGA GAT CGC TAC     348
Leu Asp Pro Ser Glu Ala Gly Pro Pro Arg Tyr Leu Gly Asp Arg Tyr
                 85                  90                  95

AAG TTT TAT CTG GAG AAT CTC ACC CTG GGG ATA CGG GAA AGC AGG AAG     396

-continued

```
       Lys Phe Tyr Leu Glu Asn Leu Thr Leu Gly Ile Arg Glu Ser Arg Lys
                       100                 105                 110

GAG GAT GAG GGA TGG TAC CTT ATG ACC CTG GAG AAA AAT GTT TCA GTT          444
Glu Asp Glu Gly Trp Tyr Leu Met Thr Leu Glu Lys Asn Val Ser Val
            115                 120                 125

CAG CGC TTT TGC CTG CAG TTG AGG CTT TAT GAG CAG GTC TCC ACT CCA          492
Gln Arg Phe Cys Leu Gln Leu Arg Leu Tyr Glu Gln Val Ser Thr Pro
        130                 135                 140

GAA ATT AAA GTT TTA AAC AAG ACC CAG GAG AAC GGG ACC TGC ACC TTG          540
Glu Ile Lys Val Leu Asn Lys Thr Gln Glu Asn Gly Thr Cys Thr Leu
145                 150                 155                 160

ATA CTG GGC TGC ACA GTG GAG AAG GGG GAC CAT GTG GCT TAC AGC TGG          588
Ile Leu Gly Cys Thr Val Glu Lys Gly Asp His Val Ala Tyr Ser Trp
                165                 170                 175

AGT GAA AAG GCG GGC ACC CAC CCA CTG AAC CCA GCC AAC AGC TCC CAC          636
Ser Glu Lys Ala Gly Thr His Pro Leu Asn Pro Ala Asn Ser Ser His
            180                 185                 190

CTC CTG TCC CTC ACC CTC GGC CCC CAG CAT GCT GAC AAT ATC TAC ATC          684
Leu Leu Ser Leu Thr Leu Gly Pro Gln His Ala Asp Asn Ile Tyr Ile
        195                 200                 205

TGC ACC GTG AGC AAC CCT ATC AGC AAC AAT TCC CAG ACC TTC AGC CCG          732
Cys Thr Val Ser Asn Pro Ile Ser Asn Asn Ser Gln Thr Phe Ser Pro
210                 215                 220

TGG CCC GGA TGC AGG ACA GAC CCC TCA GGT AAA ACG AAC CAT TAC CAG          780
Trp Pro Gly Cys Arg Thr Asp Pro Ser Gly Lys Thr Asn His Tyr Gln
225                 230                 235                 240

ACA ACA GTG GAA AAA AAA AGC CTT ACG ATC TAT GCC CAA GTC CAG AAA          828
Thr Thr Val Glu Lys Lys Ser Leu Thr Ile Tyr Ala Gln Val Gln Lys
                245                 250                 255

CCA GGT CCT CTT CAG AAG AAA CTT GAC TCC TTC CCA GCT CAG GAC CCT          876
Pro Gly Pro Leu Gln Lys Lys Leu Asp Ser Phe Pro Ala Gln Asp Pro
            260                 265                 270

TGC ACC ACC ATA TAT GTT GCT GCC ACA GAG CCT GTC CCA GAG TCT GTC          924
Cys Thr Thr Ile Tyr Val Ala Ala Thr Glu Pro Val Pro Glu Ser Val
        275                 280                 285

CAG GAA ACA AAT TCC ATC ACA GTC TAT GCT AGT GTG ACA CTT CCA GAG          972
Gln Glu Thr Asn Ser Ile Thr Val Tyr Ala Ser Val Thr Leu Pro Glu
290                 295                 300

AGC TGACACCAGA GACCAACAAA GGGACTTTCT GAAGGAAAAT GGAAA                   1020
Ser
305
```

(2) INFORMATION FOR SEQ ID NO:6:

(i) SEQUENCE CHARACTERISTICS:
        (A) LENGTH: 305 amino acids
        (B) TYPE: amino acid
        (D) TOPOLOGY: linear (ii) MOLECULE TYPE: protein (xi) SEQUENCE DESCRIPTION: SEQ ID NO:6:

```
Met Asp Pro Lys Gly Leu Leu Ser Leu Thr Phe Val Leu Phe Leu Ser
1               5                   10                  15

Leu Ala Phe Gly Ala Ser Tyr Gly Thr Gly Gly Arg Met Met Asn Cys
            20                  25                  30

Pro Lys Ile Leu Arg Gln Leu Gly Ser Lys Val Leu Leu Pro Leu Thr
        35                  40                  45

Tyr Glu Arg Ile Asn Lys Ser Met Asn Lys Ser Ile His Ile Val Val
    50                  55                  60

Thr Met Ala Lys Ser Leu Glu Asn Ser Val Glu Asn Lys Ile Val Ser
```

```
           65                  70                  75                  80
Leu Asp Pro Ser Glu Ala Gly Pro Pro Arg Tyr Leu Gly Asp Arg Tyr
                    85                  90                  95

Lys Phe Tyr Leu Glu Asn Leu Thr Leu Gly Ile Arg Glu Ser Arg Lys
                100                 105                 110

Glu Asp Glu Gly Trp Tyr Leu Met Thr Leu Glu Lys Asn Val Ser Val
            115                 120                 125

Gln Arg Phe Cys Leu Gln Leu Arg Leu Tyr Glu Gln Val Ser Thr Pro
    130                 135                 140

Glu Ile Lys Val Leu Asn Lys Thr Gln Glu Asn Gly Thr Cys Thr Leu
145                 150                 155                 160

Ile Leu Gly Cys Thr Val Glu Lys Gly Asp His Val Ala Tyr Ser Trp
                165                 170                 175

Ser Glu Lys Ala Gly Thr His Pro Leu Asn Pro Ala Asn Ser Ser His
                180                 185                 190

Leu Leu Ser Leu Thr Leu Gly Pro Gln His Ala Asp Asn Ile Tyr Ile
            195                 200                 205

Cys Thr Val Ser Asn Pro Ile Ser Asn Asn Ser Gln Thr Phe Ser Pro
    210                 215                 220

Trp Pro Gly Cys Arg Thr Asp Pro Ser Gly Lys Thr Asn His Tyr Gln
225                 230                 235                 240

Thr Thr Val Glu Lys Lys Ser Leu Thr Ile Tyr Ala Gln Val Gln Lys
                245                 250                 255

Pro Gly Pro Leu Gln Lys Lys Leu Asp Ser Phe Pro Ala Gln Asp Pro
                260                 265                 270

Cys Thr Thr Ile Tyr Val Ala Ala Thr Glu Pro Val Pro Glu Ser Val
    275                 280                 285

Gln Glu Thr Asn Ser Ile Thr Val Tyr Ala Ser Val Thr Leu Pro Glu
    290                 295                 300

Ser
305

(2) INFORMATION FOR SEQ ID NO:7:

(i) SEQUENCE CHARACTERISTICS:
        (A) LENGTH: 1079 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 153..1073

(xi) SEQUENCE DESCRIPTION: SEQ ID NO:7:

GGACTCTGTT CCTGTCTTTC TGTCTATCTT CTTCCCAAGG CAGGCTATTG CTTTCTGTTT      60

AGAAGTATCA GGGCTATGAG AAAAGGTATT TGAGAAAGAA AAAGCCAAGC AAGAAGTGGA     120

CTTTGGACTG CCTGTGTGAG TGGGGTGGGC GC ATG ATG AAC TGC CCA AAG ATT      173
                                   Met Met Asn Cys Pro Lys Ile
                                    1               5

CTC CGG CAG TTG GGA AGC AAA GTG CTG CTG CCC CTG ACA TAT GAA AGG      221
Leu Arg Gln Leu Gly Ser Lys Val Leu Leu Pro Leu Thr Tyr Glu Arg
        10                  15                  20

ATA AAT AAG AGC ATG AAC AAA AGC ATC CAC ATT GTC GTC ACA ATG GCA      269
Ile Asn Lys Ser Met Asn Lys Ser Ile His Ile Val Val Thr Met Ala
    25                  30                  35
```

| | | | | | | | | | | | | | | | | |
|---|---|---|---|---|---|---|---|---|---|---|---|---|---|---|---|---|
| AAA | TCA | CTG | GAG | AAC | AGT | GTC | GAG | AAC | AAA | ATA | GTG | TCT | CTT | GAT | CCA | 317 |
| Lys | Ser | Leu | Glu | Asn | Ser | Val | Glu | Asn | Lys | Ile | Val | Ser | Leu | Asp | Pro | |
| 40 | | | | | 45 | | | | 50 | | | | | | 55 | |
| TCC | GAA | GCA | GGC | CCT | CCA | CGT | TAT | CTA | GGA | GAT | CGC | TAC | AAG | TTT | TAT | 365 |
| Ser | Glu | Ala | Gly | Pro | Pro | Arg | Tyr | Leu | Gly | Asp | Arg | Tyr | Lys | Phe | Tyr | |
| | | | 60 | | | | | 65 | | | | | 70 | | | |
| CTG | GAG | AAT | CTC | ACC | CTG | GGG | ATA | CGG | GAA | AGC | AGG | AAG | GAG | GAT | GAG | 413 |
| Leu | Glu | Asn | Leu | Thr | Leu | Gly | Ile | Arg | Glu | Ser | Arg | Lys | Glu | Asp | Glu | |
| | | 75 | | | | | 80 | | | | | 85 | | | | |
| GGA | TGG | TAC | CTT | ATG | ACC | CTG | GAG | AAA | AAT | GTT | TCA | GTT | CAG | CGC | TTT | 461 |
| Gly | Trp | Tyr | Leu | Met | Thr | Leu | Glu | Lys | Asn | Val | Ser | Val | Gln | Arg | Phe | |
| | | 90 | | | | | 95 | | | | | 100 | | | | |
| TGC | CTG | CAG | TTG | AGG | CTT | TAT | GAG | CAG | GTC | TCC | ACT | CCA | GAA | ATT | AAA | 509 |
| Cys | Leu | Gln | Leu | Arg | Leu | Tyr | Glu | Gln | Val | Ser | Thr | Pro | Glu | Ile | Lys | |
| | 105 | | | | 110 | | | | | 115 | | | | | | |
| GTT | TTA | AAC | AAG | ACC | CAG | GAG | AAC | GGG | ACC | TGC | ACC | TTG | ATA | CTG | GGC | 557 |
| Val | Leu | Asn | Lys | Thr | Gln | Glu | Asn | Gly | Thr | Cys | Thr | Leu | Ile | Leu | Gly | |
| 120 | | | | 125 | | | | | 130 | | | | | | 135 | |
| TGC | ACA | GTG | GAG | AAG | GGG | GAC | CAT | GTG | GCT | TAC | AGC | TGG | AGT | GAA | AAG | 605 |
| Cys | Thr | Val | Glu | Lys | Gly | Asp | His | Val | Ala | Tyr | Ser | Trp | Ser | Glu | Lys | |
| | | | 140 | | | | | 145 | | | | | 150 | | | |
| GCG | GGC | ACC | CAC | CCA | CTG | AAC | CCA | GCC | AAC | AGC | TCC | CAC | CTC | CTG | TCC | 653 |
| Ala | Gly | Thr | His | Pro | Leu | Asn | Pro | Ala | Asn | Ser | Ser | His | Leu | Leu | Ser | |
| | | 155 | | | | | 160 | | | | | 165 | | | | |
| CTC | ACC | CTC | GGC | CCC | CAG | CAT | GCT | GAC | AAT | ATC | TAC | ATC | TGC | ACC | GTG | 701 |
| Leu | Thr | Leu | Gly | Pro | Gln | His | Ala | Asp | Asn | Ile | Tyr | Ile | Cys | Thr | Val | |
| | 170 | | | | | 175 | | | | | 180 | | | | | |
| AGC | AAC | CCT | ATC | AGC | AAC | AAT | TCC | CAG | ACC | TTC | AGC | CCG | TGG | CCC | GGA | 749 |
| Ser | Asn | Pro | Ile | Ser | Asn | Asn | Ser | Gln | Thr | Phe | Ser | Pro | Trp | Pro | Gly | |
| 185 | | | | | 190 | | | | | 195 | | | | | | |
| TGC | AGG | ACA | GAC | CCC | TCA | GAA | ACA | AAA | CCA | TGG | GCA | GTG | TAT | GCT | GGG | 797 |
| Cys | Arg | Thr | Asp | Pro | Ser | Glu | Thr | Lys | Pro | Trp | Ala | Val | Tyr | Ala | Gly | |
| 200 | | | | 205 | | | | | 210 | | | | | 215 | | |
| CTG | TTA | GGG | GGT | GTC | ATC | ATG | ATT | CTC | ATC | ATG | GTG | GTA | ATA | CTA | CAG | 845 |
| Leu | Leu | Gly | Gly | Val | Ile | Met | Ile | Leu | Ile | Met | Val | Val | Ile | Leu | Gln | |
| | | | 220 | | | | | 225 | | | | | 230 | | | |
| TTG | AGA | AGA | AGA | GGT | AAA | ACG | AAC | CAT | TAC | CAG | ACA | ACA | GTG | GAA | AAA | 893 |
| Leu | Arg | Arg | Arg | Gly | Lys | Thr | Asn | His | Tyr | Gln | Thr | Thr | Val | Glu | Lys | |
| | 235 | | | | | 240 | | | | | 245 | | | | | |
| AAA | AGC | CTT | ACG | ATC | TAT | GCC | CAA | GTC | CAG | AAA | CCA | GGT | CCT | CTT | CAG | 941 |
| Lys | Ser | Leu | Thr | Ile | Tyr | Ala | Gln | Val | Gln | Lys | Pro | Gly | Pro | Leu | Gln | |
| | | 250 | | | | | 255 | | | | | 260 | | | | |
| AAG | AAA | CTT | GAC | TCC | TTC | CCA | GCT | CAG | GAC | CCT | TGC | ACC | ACC | ATA | TAT | 989 |
| Lys | Lys | Leu | Asp | Ser | Phe | Pro | Ala | Gln | Asp | Pro | Cys | Thr | Thr | Ile | Tyr | |
| 265 | | | | | 270 | | | | | 275 | | | | | | |
| GTT | GCT | GCC | ACA | GAG | CCT | GTC | CCA | GAG | TCT | GTC | CAG | GAA | ACA | AAT | TCC | 1037 |
| Val | Ala | Ala | Thr | Glu | Pro | Val | Pro | Glu | Ser | Val | Gln | Glu | Thr | Asn | Ser | |
| 280 | | | | 285 | | | | | 290 | | | | | 295 | | |
| ATC | ACA | GTC | TAT | GCT | AGT | GTG | ACA | CTT | CCA | GAG | AGC | TGACAC | | | | 1079 |
| Ile | Thr | Val | Tyr | Ala | Ser | Val | Thr | Leu | Pro | Glu | Ser | | | | | |
| | | | 300 | | | | | 305 | | | | | | | | |

(2) INFORMATION FOR SEQ ID NO:8:

(i) SEQUENCE CHARACTERISTICS:
        (A) LENGTH: 307 amino acids
        (B) TYPE: amino acid
        (D) TOPOLOGY: linear (ii) MOLECULE TYPE: protein (xi) SEQUENCE DESCRIPTION: SEQ ID NO:8:

```
Met Met Asn Cys Pro Lys Ile Leu Arg Gln Leu Gly Ser Lys Val Leu
1               5                   10                  15

Leu Pro Leu Thr Tyr Glu Arg Ile Asn Lys Ser Met Asn Lys Ser Ile
            20                  25                  30

His Ile Val Val Thr Met Ala Lys Ser Leu Glu Asn Ser Val Glu Asn
            35                  40                  45

Lys Ile Val Ser Leu Asp Pro Ser Glu Ala Gly Pro Pro Arg Tyr Leu
50                  55                  60

Gly Asp Arg Tyr Lys Phe Tyr Leu Glu Asn Leu Thr Leu Gly Ile Arg
65                  70                  75                  80

Glu Ser Arg Lys Glu Asp Glu Gly Trp Tyr Leu Met Thr Leu Glu Lys
                85                  90                  95

Asn Val Ser Val Gln Arg Phe Cys Leu Gln Leu Arg Leu Tyr Glu Gln
                100                 105                 110

Val Ser Thr Pro Glu Ile Lys Val Leu Asn Lys Thr Gln Glu Asn Gly
                115                 120                 125

Thr Cys Thr Leu Ile Leu Gly Cys Thr Val Glu Lys Gly Asp His Val
130                 135                 140

Ala Tyr Ser Trp Ser Glu Lys Ala Gly Thr His Pro Leu Asn Pro Ala
145                 150                 155                 160

Asn Ser Ser His Leu Leu Ser Leu Thr Leu Gly Pro Gln His Ala Asp
                165                 170                 175

Asn Ile Tyr Ile Cys Thr Val Ser Asn Pro Ile Ser Asn Asn Ser Gln
                180                 185                 190

Thr Phe Ser Pro Trp Pro Gly Cys Arg Thr Asp Pro Ser Glu Thr Lys
                195                 200                 205

Pro Trp Ala Val Tyr Ala Gly Leu Leu Gly Val Ile Met Ile Leu
210                 215                 220

Ile Met Val Val Ile Leu Gln Leu Arg Arg Arg Gly Lys Thr Asn His
225                 230                 235                 240

Tyr Gln Thr Thr Val Glu Lys Lys Ser Leu Thr Ile Tyr Ala Gln Val
                245                 250                 255

Gln Lys Pro Gly Pro Leu Gln Lys Lys Leu Asp Ser Phe Pro Ala Gln
                260                 265                 270

Asp Pro Cys Thr Thr Ile Tyr Val Ala Ala Thr Glu Pro Val Pro Glu
                275                 280                 285

Ser Val Gln Glu Thr Asn Ser Ile Thr Val Tyr Ala Ser Val Thr Leu
290                 295                 300

Pro Glu Ser
305

(2) INFORMATION FOR SEQ ID NO:9:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 61..1089

(xi) SEQUENCE DESCRIPTION: SEQ ID NO:9:

TCCTGCCGAG CTGAGCTGAG CTGAGCTCAC AGCTGGGACC CTGTCTGCGA TTGCTGGCTA        60

ATG GAT CCC AAA GGA TCC CTT TCC TGG AGA ATA CTT CTG TTT CTC TCC        108
```

```
        Met Asp Pro Lys Gly Ser Leu Ser Trp Arg Ile Leu Leu Phe Leu Ser
        1               5                   10                  15

CTG GCT TTT GAG TTG AGC TAC GGA ACA GGT GGA GGT GTG ATG GAT TGC        156
Leu Ala Phe Glu Leu Ser Tyr Gly Thr Gly Gly Gly Val Met Asp Cys
            20                  25                  30

CCA GTG ATT CTC CAG AAG CTG GGA CAG GAC ACG TGG CTG CCC CTG ACG        204
Pro Val Ile Leu Gln Lys Leu Gly Gln Asp Thr Trp Leu Pro Leu Thr
                35                  40                  45

AAT GAA CAT CAG ATA AAT AAG AGC GTG AAC AAA AGT GTC CGC ATC CTC        252
Asn Glu His Gln Ile Asn Lys Ser Val Asn Lys Ser Val Arg Ile Leu
        50                  55                  60

GTC ACC ATG GCG ACG TCC CCA GGA AGC AAA TCC AAC AAG AAA ATT GTG        300
Val Thr Met Ala Thr Ser Pro Gly Ser Lys Ser Asn Lys Lys Ile Val
65                  70                  75                  80

TCT TTT GAT CTC TCT AAA GGG AGC TAT CCA GAT CAC CTG GAG GAT GGC        348
Ser Phe Asp Leu Ser Lys Gly Ser Tyr Pro Asp His Leu Glu Asp Gly
                85                  90                  95

TAC CAC TTT CAA TCG AAA AAC CTG AGC CTG AAG ATC CTC GGG AAC AGG        396
Tyr His Phe Gln Ser Lys Asn Leu Ser Leu Lys Ile Leu Gly Asn Arg
                100                 105                 110

CGG GAG AGT GAA GGA TGG TAC TTG GTG AGC GTG GAG GAG AAC GTT TCT        444
Arg Glu Ser Glu Gly Trp Tyr Leu Val Ser Val Glu Glu Asn Val Ser
            115                 120                 125

GTT CAG CAA TTC TGC AAG CAG CTG AAG CTT TAT GAA CAG GTC TCC CCT        492
Val Gln Gln Phe Cys Lys Gln Leu Lys Leu Tyr Glu Gln Val Ser Pro
        130                 135                 140

CCA GAG ATT AAA GTG CTA AAC AAA ACC CAG GAG AAC GAG AAT GGG ACC        540
Pro Glu Ile Lys Val Leu Asn Lys Thr Gln Glu Asn Glu Asn Gly Thr
145                 150                 155                 160

TGC AGC TTG CTG TTG GCC TGC ACA GTG AAG AAA GGG GAC CAT GTG ACT        588
Cys Ser Leu Leu Leu Ala Cys Thr Val Lys Lys Gly Asp His Val Thr
                165                 170                 175

TAC AGC TGG AGT GAT GAG GCA GGC ACC CAC CTG CTG AGC CGA GCC AAC        636
Tyr Ser Trp Ser Asp Glu Ala Gly Thr His Leu Leu Ser Arg Ala Asn
                180                 185                 190

CGC TCC CAC CTC CTG CAC ATC ACT CTT AGC AAC CAG CAT CAA GAC AGC        684
Arg Ser His Leu Leu His Ile Thr Leu Ser Asn Gln His Gln Asp Ser
            195                 200                 205

ATC TAC AAC TGC ACC GCA AGC AAC CCT GTC AGC AGT ATC TCT AGG ACC        732
Ile Tyr Asn Cys Thr Ala Ser Asn Pro Val Ser Ser Ile Ser Arg Thr
210                 215                 220

TTC AAC CTA TCA TCG CAA GCA TGC AAG CAG GAA TCC TCC TCA GAA TCG        780
Phe Asn Leu Ser Ser Gln Ala Cys Lys Gln Glu Ser Ser Ser Glu Ser
225                 230                 235                 240

AGT CCA TGG ATG CAA TAT ACT CTT GTA CCA CTG GGG GTC GTT ATA ATC        828
Ser Pro Trp Met Gln Tyr Thr Leu Val Pro Leu Gly Val Val Ile Ile
                245                 250                 255

TTC ATC CTG GTT TTC ACG GCA ATA ATA ATG ATG AAA AGA CAA GGT AAA        876
Phe Ile Leu Val Phe Thr Ala Ile Ile Met Met Lys Arg Gln Gly Lys
                260                 265                 270

TCA AAT CAC TGC CAG CCA CCA GTG GAA GAA AAA AGC CTT ACT ATT TAT        924
Ser Asn His Cys Gln Pro Pro Val Glu Glu Lys Ser Leu Thr Ile Tyr
            275                 280                 285

GCC CAA GTA CAG AAA TCA GGG CCT CAA GAG AAG AAA CTT CAT GAT GCC        972
Ala Gln Val Gln Lys Ser Gly Pro Gln Glu Lys Lys Leu His Asp Ala
        290                 295                 300

CTA ACA GAT CAG GAC CCC TGC ACA ACC ATT TAT GTG GCT GCC ACA GAG        1020
Leu Thr Asp Gln Asp Pro Cys Thr Thr Ile Tyr Val Ala Ala Thr Glu
305                 310                 315                 320

CCT GCC CCA GAG TCT GTC CAG GAA CCA AAC CCC ACC ACA GTT TAT GCC        1068
```

```
Pro Ala Pro Glu Ser Val Gln Glu Pro Asn Pro Thr Thr Val Tyr Ala
            325                 330                 335

AGT GTG ACA CTG CCA GAG AGC TGACCCATAT ACCCAGTGAA AGGACTTTTT      1119
Ser Val Thr Leu Pro Glu Ser
            340

GAAGGAGGAT AGAAGAACCA AAATCCACAC TGAACTGGAC CCCGGGGTCC AAGTTCTCTG  1179

TGACAGAAAC TGCACATCTG T                                           1200

(2) INFORMATION FOR SEQ ID NO:10:

(i) SEQUENCE CHARACTERISTICS:
        (A) LENGTH: 343 amino acids
        (B) TYPE: amino acid
        (D) TOPOLOGY: linear (ii) MOLECULE TYPE: protein (xi) SEQUENCE DESCRIPTION: SEQ ID NO:10:

Met Asp Pro Lys Gly Ser Leu Ser Trp Arg Ile Leu Leu Phe Leu Ser
 1               5                  10                  15

Leu Ala Phe Glu Leu Ser Tyr Gly Thr Gly Gly Gly Val Met Asp Cys
                20                  25                  30

Pro Val Ile Leu Gln Lys Leu Gly Gln Asp Thr Trp Leu Pro Leu Thr
            35                  40                  45

Asn Glu His Gln Ile Asn Lys Ser Val Asn Lys Ser Val Arg Ile Leu
        50                  55                  60

Val Thr Met Ala Thr Ser Pro Gly Ser Lys Ser Asn Lys Lys Ile Val
 65                  70                  75                  80

Ser Phe Asp Leu Ser Lys Gly Ser Tyr Pro Asp His Leu Glu Asp Gly
                85                  90                  95

Tyr His Phe Gln Ser Lys Asn Leu Ser Leu Lys Ile Leu Gly Asn Arg
                100                 105                 110

Arg Glu Ser Glu Gly Trp Tyr Leu Val Ser Val Glu Glu Asn Val Ser
            115                 120                 125

Val Gln Gln Phe Cys Lys Gln Leu Lys Leu Tyr Glu Gln Val Ser Pro
        130                 135                 140

Pro Glu Ile Lys Val Leu Asn Lys Thr Gln Glu Asn Glu Asn Gly Thr
145                 150                 155                 160

Cys Ser Leu Leu Leu Ala Cys Thr Val Lys Lys Gly Asp His Val Thr
                165                 170                 175

Tyr Ser Trp Ser Asp Glu Ala Gly Thr His Leu Leu Ser Arg Ala Asn
            180                 185                 190

Arg Ser His Leu Leu His Ile Thr Leu Ser Asn Gln His Gln Asp Ser
        195                 200                 205

Ile Tyr Asn Cys Thr Ala Ser Asn Pro Val Ser Ser Ile Ser Arg Thr
    210                 215                 220

Phe Asn Leu Ser Ser Gln Ala Cys Lys Gln Glu Ser Ser Ser Glu Ser
225                 230                 235                 240

Ser Pro Trp Met Gln Tyr Thr Leu Val Pro Leu Gly Val Val Ile Ile
                245                 250                 255

Phe Ile Leu Val Phe Thr Ala Ile Ile Met Met Lys Arg Gln Gly Lys
            260                 265                 270

Ser Asn His Cys Gln Pro Pro Val Glu Glu Lys Ser Leu Thr Ile Tyr
        275                 280                 285

Ala Gln Val Gln Lys Ser Gly Pro Gln Glu Lys Lys Leu His Asp Ala
    290                 295                 300
```

```
Leu Thr Asp Gln Asp Pro Cys Thr Thr Ile Tyr Val Ala Ala Thr Glu
305                 310                 315                 320

Pro Ala Pro Glu Ser Val Gln Glu Pro Asn Pro Thr Thr Val Tyr Ala
                325                 330                 335

Ser Val Thr Leu Pro Glu Ser
                340

(2) INFORMATION FOR SEQ ID NO:11:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 61..1047

(xi) SEQUENCE DESCRIPTION: SEQ ID NO:11:

TCCTGCCGAG CTGAGCTGAG CTGAGCTCAC AGCTGGGACC CTGTCTGCGA TTGCTGGCTA        60

ATG GAT CCC AAA GGA TCC CTT TCC TGG AGA ATA CTT CTG TTT CTC TCC        108
Met Asp Pro Lys Gly Ser Leu Ser Trp Arg Ile Leu Leu Phe Leu Ser
 1               5                  10                  15

CTG GCT TTT GAG TTG AGC TAC GGA ACA GGT GGA GGT GTG ATG GAT TGC        156
Leu Ala Phe Glu Leu Ser Tyr Gly Thr Gly Gly Gly Val Met Asp Cys
             20                  25                  30

CCA GTG ATT CTC CAG AAG CTG GGA CAG GAC ACG TGG CTG CCC CTG ACG        204
Pro Val Ile Leu Gln Lys Leu Gly Gln Asp Thr Trp Leu Pro Leu Thr
         35                  40                  45

AAT GAA CAT CAG ATA AAT AAG AGC GTG AAC AAA AGT GTC CGC ATC CTC        252
Asn Glu His Gln Ile Asn Lys Ser Val Asn Lys Ser Val Arg Ile Leu
     50                  55                  60

GTC ACC ATG GCG ACG TCC CCA GGA AGC AAA TCC AAC AAG AAA ATT GTG        300
Val Thr Met Ala Thr Ser Pro Gly Ser Lys Ser Asn Lys Lys Ile Val
 65                  70                  75                  80

TCT TTT GAT CTC TCT AAA GGG AGC TAT CCA GAT CAC CTG GAG GAT GGC        348
Ser Phe Asp Leu Ser Lys Gly Ser Tyr Pro Asp His Leu Glu Asp Gly
             85                  90                  95

TAC CAC TTT CAA TCG AAA AAC CTG AGC CTG AAG ATC CTC GGG AAC AGG        396
Tyr His Phe Gln Ser Lys Asn Leu Ser Leu Lys Ile Leu Gly Asn Arg
            100                 105                 110

CGG GAG AGT GAA GGA TGG TAC TTG GTG AGC GTG GAG GAG AAC GTT TCT        444
Arg Glu Ser Glu Gly Trp Tyr Leu Val Ser Val Glu Glu Asn Val Ser
        115                 120                 125

GTT CAG CAA TTC TGC AAG CAG CTG AAG CTT TAT GAA CAG GTC TCC CCT        492
Val Gln Gln Phe Cys Lys Gln Leu Lys Leu Tyr Glu Gln Val Ser Pro
    130                 135                 140

CCA GAG ATT AAA GTG CTA AAC AAA ACC CAG GAG AAC GAG AAT GGG ACC        540
Pro Glu Ile Lys Val Leu Asn Lys Thr Gln Glu Asn Glu Asn Gly Thr
145                 150                 155                 160

TGC AGC TTG CTG TTG GCC TGC ACA GTG AAG AAA GGG GAC CAT GTG ACT        588
Cys Ser Leu Leu Leu Ala Cys Thr Val Lys Lys Gly Asp His Val Thr
                165                 170                 175

TAC AGC TGG AGT GAT GAG GCA GGC ACC CAC CTG CTG AGC CGA GCC AAC        636
Tyr Ser Trp Ser Asp Glu Ala Gly Thr His Leu Leu Ser Arg Ala Asn
            180                 185                 190

CGC TCC CAC CTC CTG CAC ATC ACT CTT AGC AAC CAG CAT CAA GAC AGC        684
Arg Ser His Leu Leu His Ile Thr Leu Ser Asn Gln His Gln Asp Ser
        195                 200                 205
```

```
ATC TAC AAC TGC ACC GCA AGC AAC CCT GTC AGC AGT ATC TCT AGG ACC      732
Ile Tyr Asn Cys Thr Ala Ser Asn Pro Val Ser Ser Ile Ser Arg Thr
210                 215                 220

TTC AAC CTA TCA TCG CAA GCA TGC AAG CAG GAA TCC TCC TCA GAA TCG      780
Phe Asn Leu Ser Ser Gln Ala Cys Lys Gln Glu Ser Ser Ser Glu Ser
225                 230                 235                 240

AGT CCA TGG ATG CAA TAT ACT CTT GTA CCA CTG GGG GTC GTT ATA ATC      828
Ser Pro Trp Met Gln Tyr Thr Leu Val Pro Leu Gly Val Val Ile Ile
                245                 250                 255

TTC ATC CTG GTT TTC ACG GCA ATA ATA ATG ATG AAA AGA CAA GGT AAA      876
Phe Ile Leu Val Phe Thr Ala Ile Ile Met Met Lys Arg Gln Gly Lys
            260                 265                 270

TCA AAT CAC TGC CAG CCA CCA GTG GAA GAA AAA AGC CTT ACT ATT TAT      924
Ser Asn His Cys Gln Pro Pro Val Glu Glu Lys Ser Leu Thr Ile Tyr
        275                 280                 285

GCC CAA GTA CAG AAA TCA GGG GTA CGT TCT ATG CCT CAC CTT GCG GGA      972
Ala Gln Val Gln Lys Ser Gly Val Arg Ser Met Pro His Leu Ala Gly
    290                 295                 300

GTG TCT GTC ATA TTT CGC ACA GGA TTT CTG ATA GCT GCC TTG CAC ACA     1020
Val Ser Val Ile Phe Arg Thr Gly Phe Leu Ile Ala Ala Leu His Thr
305                 310                 315                 320

ACC ATG GTC CTG CAG GGA CTC CTA GAG TAGATGAACT TAAGAAAGCA           1067
Thr Met Val Leu Gln Gly Leu Leu Glu
                325

GAAAAGTCAA GAACAAGAGC TCCCCCAGTG TCACTGACCC TTATATTGTT TGAACTTGTA   1127

GAAAACAGTG ACA                                                      1140

(2) INFORMATION FOR SEQ ID NO:12:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:12:

Met Asp Pro Lys Gly Ser Leu Ser Trp Arg Ile Leu Leu Phe Leu Ser
 1               5                  10                  15

Leu Ala Phe Glu Leu Ser Tyr Gly Thr Gly Gly Gly Val Met Asp Cys
                20                  25                  30

Pro Val Ile Leu Gln Lys Leu Gly Gln Asp Thr Trp Leu Pro Leu Thr
            35                  40                  45

Asn Glu His Gln Ile Asn Lys Ser Val Asn Lys Ser Val Arg Ile Leu
        50                  55                  60

Val Thr Met Ala Thr Ser Pro Gly Ser Lys Ser Asn Lys Lys Ile Val
65                  70                  75                  80

Ser Phe Asp Leu Ser Lys Gly Ser Tyr Pro Asp His Leu Glu Asp Gly
                85                  90                  95

Tyr His Phe Gln Ser Lys Asn Leu Ser Leu Lys Ile Leu Gly Asn Arg
                100                 105                 110

Arg Glu Ser Glu Gly Trp Tyr Leu Val Ser Val Glu Glu Asn Val Ser
            115                 120                 125

Val Gln Gln Phe Cys Lys Gln Leu Lys Leu Tyr Glu Gln Val Ser Pro
    130                 135                 140

Pro Glu Ile Lys Val Leu Asn Lys Thr Gln Glu Asn Glu Asn Gly Thr
145                 150                 155                 160

Cys Ser Leu Leu Leu Ala Cys Thr Val Lys Lys Gly Asp His Val Thr
                165                 170                 175
```

```
Tyr Ser Trp Ser Asp Glu Ala Gly Thr His Leu Leu Ser Arg Ala Asn
        180                 185                 190

Arg Ser His Leu Leu His Ile Thr Leu Ser Asn Gln His Gln Asp Ser
        195                 200                 205

Ile Tyr Asn Cys Thr Ala Ser Asn Pro Val Ser Ser Ile Ser Arg Thr
    210                 215                 220

Phe Asn Leu Ser Ser Gln Ala Cys Lys Gln Glu Ser Ser Ser Glu Ser
225             230                 235                 240

Ser Pro Trp Met Gln Tyr Thr Leu Val Pro Leu Gly Val Val Ile Ile
            245                 250                 255

Phe Ile Leu Val Phe Thr Ala Ile Ile Met Met Lys Arg Gln Gly Lys
            260                 265                 270

Ser Asn His Cys Gln Pro Pro Val Glu Glu Lys Ser Leu Thr Ile Tyr
        275                 280                 285

Ala Gln Val Gln Lys Ser Gly Val Arg Ser Met Pro His Leu Ala Gly
    290                 295                 300

Val Ser Val Ile Phe Arg Thr Gly Phe Leu Ile Ala Ala Leu His Thr
305                 310                 315                 320

Thr Met Val Leu Gln Gly Leu Leu Glu
                325
```

MAMMALIAN CELL SURFACE ANTIGENS

This is a divisional of application U.S. Ser. No. 08/348,792, filed on Dec. 2, 1994 now abandoned.

FIELD OF THE INVENTION

The present invention pertains to compositions related to proteins which function in controlling activation of mammalian cells, e.g., cells of a mammalian immune system. In particular, it provides purified genes, proteins, antibodies, and related reagents useful, e.g., to regulate activation, development, differentiation, and function of various cell types, including hematopoietic cells.

BACKGROUND OF THE INVENTION

The activation of resting T cells is critical to most immune responses and allows these cells to exert their regulatory or effector capabilities. See Paul (ed; 1993) *Fundamental Immunology* 3d ed., Raven Press, N.Y. Increased adhesion between T cells and antigen presenting cells (APC) or other forms of primary stimuli, e.g., immobilized monoclonal antibodies (mAb), can potentiate the T-cell receptor signals. T-cell activation and T cell expansion depends upon engagement of the T-cell receptor (TCR) and co-stimulatory signals provided by accessory cells. See, e.g., Jenkins and Johnson (1993) *Curr. Opin. Immunol.* 5:361–367; Bierer and Hahn (1993) *Semin. Immunol.* 5:249–261; June, et al. (1990) *Immunol. Today* 11:211–216; and Jenkins (1994) *Immunity* 1:443–446. A major, and well-studied, co-stimulatory interaction for T cells involves either CD28 or CTLA-4 on T cells with either B7 or B70 (Jenkins (1994) *Immunity* 1:443–446). Recent studies on CD28 deficient mice (Shahinian, et al. (1993) *Science* 261:609–612; Green, et al. (1994) *Immunity* 1:501–508) and CTLA-4 immunoglobulin expressing transgenic mice (Ronchese, et al. (1994) *J. Exp. Med.* 179:809–817) have revealed deficiencies in some T-cell responses though these mice have normal primary immune responses and normal CTL responses to lymphocytic choriomeningitis virus and vesicular stomatitis virus. As a result, both these studies conclude that other co-stimulatory molecules must be supporting T-cell function. However, identification of these molecules which mediate distinct costimulatory signals has been difficult.

The inability to modulate activation signals prevents control of inappropriate developmental or physiological responses in the immune system. The present invention provides at least one alternative costimulatory molecule, agonists and antagonists of which will be useful in modulating a plethora of immune responses.

SUMMARY OF THE INVENTION

The present invention is based, in part, upon the discovery of an antigen which acts as a costimulator of T cell activation. In particular, it provides a gene encoding a glycosylated 70 kDa protein, designated SLAM, which is expressed on CD4$^+$, CD8$^+$ thymocytes and peripheral blood CD45RO$^{high}$ memory T cells, and is rapidly induced on naive T cells following activation. Engagement of SLAM directly stimulates proliferation of CD4$^+$ T cell clones and enhances antigen-specific proliferation and cytokine production by CD4$^+$ T cells. Particularly the production of IFN-$\gamma$ is strongly upregulated, even in T helper type 2 (Th2) CD4$^+$ T cell clones, whereas no induction of IL-4 or IL-5 production was observed in Th1 clones. These data indicate SLAM is a novel T-cell co-stimulatory molecule which, when engaged, potentiates T cell expansion and induces a Th0/Th1 cytokine production profile. Both human and mouse embodiments are described, enabling mammalian genes, proteins, antibodies, and uses thereof. Functional equivalents exhibiting significant sequence homology are available from non-mammalian species. Moreover, SLAM can function as its binding partner to stimulate other cells expressing the antigen in a homophilic interaction.

More particularly, the present invention provides a substantially pure or recombinant SLAM protein or peptide fragment thereof. Various embodiments include a protein or peptide selected from a protein or peptide from a warm blooded animal selected from the group of birds and mammals, including a human or mouse; a protein or peptide comprising at least one polypeptide segment of SEQ ID NO: 2, 4, 6, 8, 10, or 12; a protein or peptide which exhibits a post-translational modification pattern distinct from natural SLAM; or a protein or peptide which is capable of co-stimulating a T cell with another signal. The protein or peptide can comprise a sequence from the extracellular or the intracellular portion of a SLAM; or be a fusion protein. Another embodiment is a composition comprising a SLAM protein and a pharmaceutically acceptable carrier.

The invention also embraces an antibody which specifically binds a SLAM protein or peptide, e.g., wherein the SLAM is a mammalian protein, including a human or mouse; the antibody is raised against a purified SLAM peptide sequence of SEQ ID NO; 2, 4, 6, 8, 10, or 12; the antibody is a monoclonal antibody; or the antibody is labeled. The antibodies also make available a method of purifying a SLAM protein or peptide from other materials in a mixture comprising contacting the mixture to an anti-SLAM antibody, and separating bound SLAM from other materials.

Another aspect of the invention is an isolated or recombinant nucleic acid capable of encoding a SLAM protein or peptide, including a nucleic acid which encodes a sequence of SEQ ID NO: 2, 4, 6, 8, 10, or 12; which includes a sequence of SEQ ID NO: 1, 3, 5, 7, 9, or 11; which encodes a sequence from an extracellular domain of a natural SLAM; or which encodes a sequence from an intracellular domain of a natural SLAM. Such nucleic acid embodiments also include an expression or replicating vector.

The invention also provides a kit containing a substantially pure SLAM or fragment; an antibody or receptor which specifically binds a SLAM; or a nucleic acid, or its complement, encoding a SLAM or peptide. This kit also provides methods for detecting in a sample the presence of a nucleic acid, protein, or antibody, comprising testing said sample with such a kit.

The invention also supplies methods of modulating the physiology of a cell comprising contacting said cell with a substantially pure SLAM or fragment; an antibody or binding partner which specifically binds a SLAM; or a nucleic acid encoding a SLAM or peptide. Certain preferred embodiments include a method where the cell is a T cell and the modulating of physiology is activation of the T cell; or where the cell is in a tissue and/or in an organism.

Also provided are a method of expressing a SLAM peptide by expressing a nucleic acid encoding a SLAM polypeptide. The invention also provides a cell, tissue, organ, or organism comprising a nucleic acid encoding a SLAM peptide.

The invention also provides a recombinant nucleic acid comprising sequence at least about 70% identity over a stretch of at least about 30 nucleotides to a SLAM nucleic acid sequence of SEQ ID NO: 1, 3, 5, 7, 9, or 11, useful, e.g., as a probe or PCR primer for a related gene. Another embodiment encodes a polypeptide comprising at least about 60% identity over a stretch of at least about 20 amino acids to a SLAM sequence of SEQ ID NO: 2, 4, 6, 8, 10, or 12.

DETAILED DESCRIPTION OF THE PREFERRED EMBODIMENTS

All references cited herein are incorporated herein by reference to the same extent as if each individual publication or patent application was specifically and individually indicated to be incorporated by reference.

OUTLINE

I. General
II. Purified SLAM
   A. physical properties
   B. biological properties
III. Physical variants
   A. sequence variants, fragments
   B. post-translational variants
   1. glycosylation
   2. others
IV. Functional Variants
   A. analogs, fragments
   1. agonists
   2. antagonists
   B. mimetics
   1. protein
   2. chemicals
   C. species variants
V. Antibodies
   A. polyclonal
   B. monoclonal
   C. fragments, binding compositions,
VI. Nucleic Acids
   A. natural isolates; methods
   B. synthetic genes
   C. methods to isolate
VII. Making SLAM, mimetics
   A. recombinant methods
   B. synthetic methods
   C. natural purification
VIII. Uses
   A. diagnostic
   B. therapeutic
IX. Kits
   A. nucleic acid reagents
   B. protein reagents
   C. antibody reagents
   I. General The present invention provides amino acid sequences and DNA sequences encoding various mammalian proteins which are antigens found in the early stages of T cell activation, e.g., which can activate a T cell. Among these proteins are antigens which induce proliferation of T cells, among other physiological effects. The full length antigens, and fragments, will be useful in both physiological modulation of cells expressing the antigen. The proteins will also be useful as antigens, e.g., immunogens, for raising antibodies to various epitopes on the protein, both linear and conformational epitopes.

Monoclonal antibodies (mAb) were raised to molecules expressed in the early phase of T-cell activation. One antibody designated A12 had unique agonistic effects on T cell clones and recognized a previously unidentified early activation molecule designated SLAM. A12 directly induced proliferation of CD4$^+$ T cell clones belonging to the Th0, Th1, and Th2-like subsets. In the absence of any other stimuli, A12 or its F(Ab')$_2$ induced proliferation of T cell clones B21, ChT38, HY06, and TA23, whereas consistent with previous studies, see June, et al. (1990) *Immunol. Today* 11:211–216, engagement of CD28 was ineffective. These data indicate that SLAM acts independently of CD28 and that it plays a novel and important role in T cell activation.

A cDNA encoding SLAM was isolated from a T-cell cDNA library by expression cloning using A12 for selection. The SLAM cDNA was 1860 bp in length and contained one large open reading frame encoding a type I transmembrane protein with a 27 amino-acid N-terminal hydrophobic leader sequence, a 202 amino-acid extracellular region which contains 8 potential N-glycosylation sites, a 22 amino-acid hydrophobic membrane spanning portion, and a 77 amino-acid cytoplasmic domain. See SEQ. ID. NO: 1. Three of the four potential tyr phosphorylation sites in the cytoplasmic domain of SLAM conform to the consensus sequence phosphotyrosine-hydrophobic-X-hydrophobic, determined for binding to one class of SH2 domains. See zhou, et al. (1993) *Cell* 72:767–778. Antisera raised against recombinant SLAM precipitated a 70 kD glycoprotein from an activated CD4$^+$ T-cell clone. N-glycanase treatment of the SLAM immunoprecipitate revealed a protein core of 40 kDa, which correlates with the predicted molecular size. SLAM exhibits characteristics of a member of the immunoglobulin (Ig) supergene family, with one variable and one constant domain, and shows some degree of homology with CD48 (26% homology; see Staunton and Thorley-Lawson (1987) *EMBO J.* 6:3695–3701), LFA-3/CD58 (17% homology; see Seed (1987) *Nature* 329:840–842), and a recently cloned signaling molecule expressed on murine NK and cytotoxic T cells called 2B4 (28% homology; see Mathew, et al. (1993) *J. Immunol.* 151:5328–5337).

Using PCR to detect transcripts in various tissues and cell types, it is clear that SLAM is expressed primarily in lymphoid cells. Activated peripheral blood mononuclear cells (PBMC) contain a 1.9 kb transcript, corresponding to the size of the cloned SLAM cDNA and also a 4 kb transcript. The 4 kb mRNA is composed of at least two different transcripts, including one encoding a secreted form of SLAM lacking 30 amino-acids, including the entire 22 amino-acid transmembrane region, and another which encodes transmembrane SLAM. An alternatively spliced 2 kb cDNA clone was also identified, encoding a form of SLAM with a truncated cytoplasmic domain.

SLAM mRNA is induced within 2 h after activation, which correlates with its rapid appearance on the T-cell surface. SLAM is not expressed on CD45RA$^+$ naive T cells, but can be detected at low levels on CD45RO$^{high}$ memory T cells in the absence of in vitro activation. SLAM expression is rapidly induced (within 3 h) on naive CD45RA$^+$ T cells and enhanced on CD45RO$^{high}$ T cells following activation, and maximal expression occurs at 6–8 h. Immature CD3$^{low}$, CD4$^+$, CD8$^+$ fetal thymocytes express SLAM, whereas the more mature CD3$^{high}$ single CD4$^+$ or CD8$^+$ thymocytes are mostly negative. SLAM is expressed at very low levels on peripheral B cells and is upregulated with activation but is not present on monocytes.

The presence of SLAM on B cells and CD45RO$^{high}$ memory T cells, and the natural occurrence of a soluble form of SLAM, suggest a broad function of this molecule. The findings that co-stimulation via SLAM enhances Ag-specific proliferative responses and induces Th0/Th1 cytokine production profiles in T cell clones, including Th2 clones, suggests that the interaction between SLAM and its ligand will contribute to T cell expansion and the generation of Th0 or Th1 responses.

In addition to its direct stimulatory effects on T cell clones, SLAM acts as a co-stimulatory molecule for T-cell activation. The optimal antigen-specific proliferative responses of peripheral blood T cells of donors immunized with tetanus toxoid (TT) or purified protein derivative (PPD) were further enhanced in a dose dependent fashion by the addition of A12 F(ab')$_2$, indicating that specific engagement of SLAM is responsible for the enhanced T-cell responses. Generally a 2–3 fold increase in proliferation was observed. Similarly, the optimal antigen-specific proliferation of CD4$^+$ T-cell clones were enhanced in the presence of A12 or A12 F(ab')$_2$ in a dose-dependent manner. This enhancement was observed with CD4$^+$ T cell clones belonging to the Th2, Th0, and Th1 subsets. The co-stimulatory effects mediated through SLAM on T cells were not restricted to Ag-specific stimulation, as T-cell proliferation induced by anti-CD3 mAb was also enhanced by A12. Even at optimal anti-CD3 concentrations, a further 2–3-fold increase in the proliferation was observed upon engagement of SLAM by A12.

Cytokine production by a panel of CD4$^+$ T-cell clones belonging to different subsets stimulated by their respective antigens was upregulated following SLAM engagement by A12. In particular, IFN-γ production was strongly enhanced by A12 and A12 F(Ab')$_2$.

Co-stimulation of Th2 clones with A12 or its F(Ab')$_2$ strongly upregulated (5–17 fold) IFN-γ production, whereas there were little (less than 2 fold), or no, enhancing effects on IL-4 production by four clones tested. The levels of IFN-γ production induced in the presence of A12 by Th2 clones were comparable to those induced by antigen in Th1 and Th0 clones. A12 co-stimulation also preferentially enhanced IFN-γ production by Th0 and Th1 clones. In contrast to its strong IFN-γ-inducing effects on Th2 clones, costimulation via SLAM did not induce IL-4 or IL-5 production by Th1 clones.

These results indicate that T cell co-stimulation via SLAM results in a preferential induction of IFN-γ production, even in allergen-specific CD4$^+$ T-cell clones of the Th2-subset, thereby reversing the phenotype of these cells to a clear Th0 cytokine production profile. The cytokine production pattern defining established Th1 clones, however, is not altered by co-stimulation via SLAM.

In order to identify the natural ligand for SLAM, a SLAM-immunoglobulin fusion protein (SLAM-Ig) was generated. The SLAM portion of SLAM-Ig bound specifically to L cells stably transfected with SLAM. In addition, SLAM-Ig interacted homophilically in solution demonstrating that SLAM can serve as a self-ligand. SLAM-Ig binding to various cell types also correlated with their SLAM expression. Unlike other described ligands for T cells, SLAM expressed on L cells provided a direct proliferative signal for human T cell clones in the absence of any other stimuli. This novel stimulatory activity provided by homophilic interaction of SLAM was resistant to cyclosporin.

TABLE 1

Human SLAM Sequences.

Human SLAM1 (pSURslam1) nucleotide and predicted amino acid sequence. Predicted leader sequence and the transmembrane sequence are underlined, though natural boundaries may be different, also depending on cell type. An exon encoding the transmembrane domain which is not present in human SLAM3 (pSECslam) is delineated by two *s and the bases bordering this exon are in bold type (nucleotides numbered 761 and 850). Cysteines are found at amino acid residues numbered 32, 132, 158, 164, 209, 228, and 303. Potential N-linked glycosylation sites are found at residues numbered 53, 57, 102, 125, 150, 155, 189, and 217. Fragments between cysteines and/or N-linked glycosylation sites are particularly useful in generating antibodies. SEQ ID NO: 1 and 2.

```
          10        20        30        40        50        60
aggcatctgtgagcagctgccaggctccggccaggatcccttccttctcctcattggctg 70        80        90       100       110       120
atggatcccaagggctcctctccttgaccttcgtgctgtttctctccctggcttttggg
 M   D   P   K   G   L   L   S   L   T   F   V   L   F   L   S   L   A   F   G
 1

130       140       150       160       170       180
gcaagctacggaacaggtgggcgcatgatgaactgcccaaagattctccggcagttggga
 A   S   Y   G   T   G   G   R   M   M   N   C   P   K   I   L   R   Q   L   G
 21

190       200       210       220       230       240
agcaaagtgctgctgcccctgacatatgaaaggataaataagagcatgaacaaaagcatc
 S   K   V   L   L   P   L   T   Y   E   R   I   N   K   S   M   N   K   S   I
 41

250       260       270       280       290       300
cacattgtcgtcacaatggcaaaatcactggagaacagtgtcgagaacaaaatagtgtct
 H   I   V   V   T   M   A   K   S   L   E   N   S   V   E   N   K   I   V   S
 61
```

TABLE 1-continued

Human SLAM Sequences.

```
         310       320       330       340       350       360
cttgatccatccgaagcaggccctccacgttatctaggagatcgctacaagttttatctg
 L  D  P  S  E  A  G  P  P  R  Y  L  G  D  R  Y  K  F  Y  L
81

370       380       390       400       410       420
gagaatctcaccctggggatacgggaaagcaggaaggaggatgagggatggtaccttatg
 E  N  L  T  L  G  I  R  E  S  R  K  E  D  E  G  W  Y  L  M
101

430       440       450       460       470       480
accctggagaaaaatgtttcagttcagcgcttttgcctgcagttgaggctttatgagcag
 T  L  E  K  N  V  S  V  Q  R  F  C  L  Q  L  R  L  Y  E  Q
121

490       500       510       520       530       540
gtctccactccagaaattaaagttttaaacaagacccaggagaacgggacctgcaccttg
 V  S  T  P  E  I  K  V  L  N  K  T  Q  E  N  G  T  C  T  L
141

550       560       570       580       590       600
atactgggctgcacagtggagaagggggaccatgtggcttacagctggagtgaaaaggcg
 I  L  G  C  T  V  E  K  G  D  H  V  A  Y  S  W  S  E  K  A
161

610       620       630       640       650       660
ggcacccacccactgaacccagccaacagctcccacctcctgtccctcaccctcggcccc
 G  T  H  P  L  N  P  A  N  S  S  H  L  L  S  L  T  L  G  P
181

670       680       690       700       710       720
cagcatgctgacaatatctacatctgcaccgtgagcaaccctatcagcaacaattcccag
 Q  H  A  D  N  I  Y  I  C  T  V  S  N  P  I  S  N  N  S  Q
201

730       740       750       760•      770       780
accttcagcccgtggcccggatgcaggacagacccctcagaaacaaaaccatgggcagtg
 T  F  S  P  W  P  G  C  R  T  D  P  S  E  T  K  P  W  A  V
221

790       800       810       820       830       840
tatgctgggctgttaggggggtgtcatcatgattctcatcatggtggtaatactacagttg
 Y  A  G  L  L  G  G  V  I  M  I  L  I  M  V  V  I  L  Q  L
241

•       860       870       880       890       900
agaagaagaggtaaaacgaaccattaccagacaacagtggaaaaaaaaagccttacgatc
 R  R  R  G  K  T  N  H  Y  Q  T  T  V  E  K  K  S  L  T  I
261

910       920       930       940       950       960
tatgcccaagtccagaaaccaggtcctcttcagaagaaacttgactccttcccagctcag
 Y  A  Q  V  Q  K  P  G  P  L  Q  K  K  L  D  S  F  P  A  Q
281

970       980       990      1000      1010      1020
gacccttgcaccaccatatatgttgctgccacagagcctgtcccagagtctgtccaggaa
 D  P  C  T  T  I  Y  V  A  A  T  E  P  V  P  E  S  V  Q  E
301

1030      1040      1050      1060      1070      1080
acaaattccatcacagtctatgctagtgtgacacttccagagagctgacaccagagacca
 T  N  S  I  T  V  Y  A  S  V  T  L  P  E  S
321

1090      1100      1110      1120      1130      1140
acaaagggactttctgaaggaaaatggaaaaaccaaaatgaacactgaacttggccacag 1150      1160      1170      1180      1190      1200
gcccaagtttcctctggcagacatgctgcacgtctgtacccttctcagatcaactccctg 1210      1220      1230      1240      1250      1260
gtgatgtttcttccacatacatctgtgaaatgaacaaggaagtgaggcttcccaagaatt 1270      1280      1290      1300      1310      1320
tagcttgctgtgcagtggctgcaggcgcagaacagagcgttacttgataacagcgttcca
```

TABLE 1-continued

Human SLAM Sequences.

```
       1330      1340      1350      1360      1370      1380
tctttgtgttgtagcagatgaaatggacagtaatgtgagttcagactttgggcatcttgc 1390      1400      1410      1420      1430      1440
tcttggctggaactgataataaaaatcagactgaaagccaggacatctgagtacctatct 1450      1460      1470      1480      1490      1500
cacacactgaccaccagtcacaaagtctggaaaagtttacattttggctatctttactt 1510      1520      1530      1540      1550      1560
gttctgggagctgatcatgataacctgcagacctgatcaagcctctgtgcctcagtttct 1570      1580      1590      1600      1610      1620
ctctcaggataaagagtgaatagaggccgaagggtgaatttcttattatacataaaacac 1630      1640      1650      1660      1670      1680
tctgatattattgtataaaggaagctaagaatattattttatttgcaaaacccagaagct 1690      1700      1710
aaaaagtcaataaacagaaagaatgattttgagaaa
```

Human SLAM2 (pSURslam2) nucleotide and predicted amino acid sequence. The human SLAM2 apparently differs from human SLAM1 by a differential splicing event resulting in a different C-terminal sequence beginning at the point indicated by • (nucleotide 924). SEQ ID NO: 3 AND 4.

```
         10        20        30        40        50        60
aggcatctgtgagcagctgccaggctccggccaggatcccttccttctcctcattggctg 70        80        90       100       110       120
atggatcccaaggggctcctctccttgaccttcgtgctgtttctctccctggcttttggg
 M   D   P   K   G   L   L   S   L   T   F   V   L   F   L   S   L   A   F   G
 1

130       140       150       160       170       180
gcaagctacggaacaggtgggcgcatgatgaactgcccaaagattctccggcagttggga
 A   S   Y   G   T   G   G   R   M   M   N   C   P   K   I   L   R   Q   L   G
 21

190       200       210       220       230       240
agcaaagtgctgctgcccctgacatatgaaaggataaataagagcatgaacaaaagcatc
 S   K   V   L   L   P   L   T   Y   E   R   I   N   K   S   M   N   K   S   I
 41

250       260       270       280       290       300
cacattgtcgtcacaatggcaaaatcactggagaacagtgtcgagaacaaaatagtgtct
 H   I   V   V   T   M   A   K   S   L   E   N   S   V   E   N   K   I   V   S
 61

310       320       330       340       350       360
cttgatccatccgaagcaggccctccacgttatctaggagatcgctacaagttttatctg
 L   D   P   S   E   A   G   P   P   R   Y   L   G   D   R   Y   K   F   Y   L
 81

370       380       390       400       410       420
gagaatctcaccctggggatacgggaaagcaggaaggaggatgagggatggtaccttatg
 E   N   L   T   L   G   I   R   E   S   R   K   E   D   E   G   W   Y   L   M
 101

430       440       450       460       470       480
accctggagaaaaatgtttcagttcagcgcttttgcctgcagttgaggctttatgagcag
 T   L   E   K   N   V   S   V   Q   R   F   C   L   Q   L   R   L   Y   E   Q
 121

490       500       510       520       530       540
gtctccactccagaaattaaagttttaaacaagacccaggagaacgggacctgcaccttg
 V   S   T   P   E   I   K   V   L   N   K   T   Q   E   N   G   T   C   T   L
 141

550       560       570       580       590       600
atactgggctgcacagtggagaaggggaccatgtggcttacagctggagtgaaaaggcg
 I   L   G   C   T   V   E   K   G   D   H   V   A   Y   S   W   S   E   K   A
 161
```

TABLE 1-continued

Human SLAM Sequences.

```
         610       620       630       640       650       660
ggcacccacccactgaacccagccaacagctcccacctcctgtccctcaccctcggcccc
  G   T   H   P   L   N   P   A   N   S   S   H   L   L   S   L   T   L   G   P
181

670       680       690       700       710       720
cagcatgctgacaatatctacatctgcaccgtgagcaaccctatcagcaacaattcccag
  Q   H   A   D   N   I   Y   I   C   T   V   S   N   P   I   S   N   N   S   Q
201

730       740       750       760       770       780
accttcagcccgtggccggatgcaggacagacccctcagaaacaaaaccatgggcagtg
  T   F   S   P   W   P   G   C   R   T   D   P   S   E   T   K   P   W   A   V
221

790       800       810       820       830       840
tatgctgggctgttaggggtgtcatcatgattctcatcatggtggtaatactacagttg
  Y   A   G   L   L   G   G   V   I   M   I   L   I   M   V   V   I   L   Q   L
241

850       860       870       880       890       900
agaagaagaggtaaaacgaaccattaccagacaacagtggaaaaaaaaagccttacgatc
  R   R   R   G   K   T   N   H   Y   Q   T   T   V   E   K   K   S   L   T   I
261

910       920    •  930       940       950       960
tatgcccaagtccagaaaccaggtgacactcatcatcagacttcggacttattctaatcc
  Y   A   Q   V   Q   K   P   G   D   T   H   H   Q   T   S   D   L   F
281

970       980       990      1000      1010      1020
aggatgaccttatttttgaaatccttatcttgacatctgtgaagacctttattcaaataaa 1030      1040      1050      1060      1070      1080
gtcacattttgacattctgcgaggggctggagccgggccggggcgatgtggagcgcgggc 1090      1100      1110      1120      1130      1140
cgcggcggggctgcctggccggtgctgttggggctgctgctggcgctgttagtgccgggc 1150      1160      1170      1180      1190      1200
ggtggtgccgccaagaccggtgcggagctcgtgactgcgggtcggtgctgaagctgctca 1210      1220      1230      1240      1250      1260
atacgcaccaccggtgcggctgcactcgcacgacatcaaatacggatccggcagcggcca 1270      1280      1290      1300      1310      1320
gcaatcggtgaccggcgtagaggtcggagcgacgaatagctactggcggatccgcggcgg 1330      1340      1350      1360      1370      1380
ctcggagggggtgcccgcgcgggtccccggtgcgctgcgggcaggcggtgaggtcacac 1390      1400      1410      1420      1430      1440
atgtgcttacgggcaagaacctgcacacgcaccacttcccgtcgccgctgtccaacaacc 1450      1460      1470      1480      1490      1500
aggaagtgagtgccaaggggaagacggcgagggcgacgacctggacctatggacagtgc 1510      1520      1530      1540      1550      1560
gctgctctgctctggacagcactgggagcgtgaggctgctgtggcgccttccagcatgtg 1570      1580      1590      1600      1610      1620
gcacctctgtggttcctgtcagtcacggtagcagtatggaagcccatccgtgggcagca 1630      1640      1650      1660      1670      1680
tgaggtccacgcatgcccagtgccaacacgcacaatacgtggaaggccatggaaggcatc 1690      1700      1710      1720      1730      1740
ttcatcaagcctagtgtggagccctctgcaggtcacgatgaactctgagtgtgtggatgg 1750      1760      1770      1780      1790      1800
atgggtggatggagggtggcaggtgggcgtctgcagggccactcttggcagagactttg 1810      1820      1830      1840      1850
ggtttgtaggggtcctcaagtgcctttgtgattaaagaatgttggtctatga
```

TABLE 1-continued

Human SLAM Sequences.

Human SLAM3 (pSECslam) nucleotide and predicted amino acid sequence. The splice junction where the transmembrane domain sequence of SLAM1 was deleted is indicated by • (nucleotide 761). SLAM3 is secreted by COS cells transfected with pSECslam, confirming that SLAM3 encodes a soluble form of SLAM for RT-PCR, the SLAM3 transcript has been detected in different cell types, confirming that it is a bonafide MRNA. SEQ ID NO: 5 and 6.

```
         10        20        30        40        50        60
aggcatctgtgagcagctgccaggctccggccaggatcccttccttctcctcattggctg 70        80        90       100       110       120
atggatcccaaggggctcctctccttgaccttcgtgctgtttctctccctggcttttggg
 M   D   P   K   G   L   L   S   L   T   F   V   L   F   L   S   L   A   F   G
 1

130       140       150       160       170       180
gcaagctacggaacaggtgggcgcatgatgaactgcccaaagattctccggcagttggga
 A   S   Y   G   T   G   G   R   M   M   N   C   P   K   I   L   R   Q   L   G
21

190       200       210       220       230       240
agcaaagtgctgctgcccctgacatatgaaaggataaataagagcatgaacaaaagcatc
 S   K   V   L   L   P   L   T   Y   E   R   I   N   K   S   M   N   K   S   I
41

250       260       270       280       290       300
cacattgtcgtcacaatggcaaaatcactggagaacagtgtcgagaacaaaatagtgtct
 H   I   V   V   T   M   A   K   S   L   E   N   S   V   E   N   K   I   V   S
61

310       320       330       340       350       360
cttgatccatccgaagcaggccctccacgttatctaggagatcgctacaagtttttatctg
 L   D   P   S   E   A   G   P   P   R   Y   L   G   D   R   Y   K   F   Y   L
81

370       380       390       400       410       420
gagaatctcaccctggggatacgggaaagcaggaaggaggatgagggatggtaccttatg
 E   N   L   T   L   G   I   R   E   S   R   K   E   D   E   G   W   Y   L   M
101

430       440       450       460       470       480
accctggagaaaaatgtttcagttcagcgcttttgcctgcagttgaggctttatgagcag
 T   L   E   K   N   V   S   V   Q   R   F   C   L   Q   L   R   L   Y   E   Q
121

490       500       510       520       530       540
gtctccactccagaaattaaagttttaaacaagacccaggagaacgggacctgcaccttg
 V   S   T   P   E   I   K   V   L   N   K   T   Q   E   N   G   T   C   T   L
141

550       560       570       580       590       600
atactgggctgcacagtggagaagggggaccatgtggcttacagctggagtgaaaaggcg
 I   L   G   C   T   V   E   K   G   D   H   V   A   Y   S   W   S   E   K   A
161

610       620       630       640       650       660
ggcacccacccactgaacccagccaacagctcccacctcctgtccctcaccctcggcccc
 G   T   H   P   L   N   P   A   N   S   S   H   L   L   S   L   T   L   G   P
181

670       680       690       700       710       720
cagcatgctgacaatatctacatctgcaccgtgagcaacccatcagcaacaattcccag
 Q   H   A   D   N   I   Y   I   C   T   V   S   N   P   I   S   N   N   S   Q
201

730       740       750         •       770       780
accttcagcccgtggcccggatgcaggacagacccctcaggtaaaacgaaccattaccag
 T   F   S   P   W   P   G   C   R   T   D   P   S   G   K   T   N   H   Y   Q
221

790       800       810       820       830       840
acaacagtggaaaaaaaaagccttacgatctatgcccaagtccagaaaccaggtcctctt
 T   T   V   E   K   K   S   L   T   I   Y   A   Q   V   Q   K   P   G   P   L
241
```

TABLE 1-continued

Human SLAM Sequences.

```
         850       860       870       880       890       900
cagaagaaacttgactccttcccagctcaggaccttgcaccaccatatatgttgctgcc
 Q   K   K   L   D   S   F   P   A   Q   D   P   C   T   T   I   Y   V   A   A
261

910       920       930       940       950       960
acagagcctgtcccagagtctgtccaggaaacaaattccatcacagtctatgctagtgtg
 T   E   P   V   P   E   S   V   Q   E   T   N   S   I   T   V   Y   A   S   V
281

970       980       990      1000      1010      1020
acacttccagagagctgacaccagagaccaacaaagggactttctgaaggaaaatggaaa
 T   L   P   E   S
301
```

Human SLAM4 (pCYTslam) nucleotide and predicted amino acid sequence. The point before which the sequence of SLAM4 differs from SLAM1 is indicated by • (nucleotide 145) and the base in bold type. The presence of this alternate exon at the 5' end predicts that SLAM4 lacks a leader sequence. The SLAM4 molecule when expressed in COS cells, is not effectively transferred to the cell surface and is presumably cytoplasmic. Using a 5' primer specific for the untranslated 5' exon of SLAM4 and a 3' primer specific for the SLAM coding region for RT-PCR, this transcript has been detected in different cell types, confirming that it a bonafide mRNA. SEQ ID NO: 7 and 8.

```
          10        20        30        40        50        60
ggactctgttcctgtctttctgtctatcttcttcccaaggcaggctattgctttctgttt 70        80        90       100       110       120
agaagtatcagggctatgagaaaaggtatttgagaaagaaaaagccaagcaaggaagtgg 130       140    •  150       160       170       180
actttggactgcctgtgtgagtggggtgggcgcatgatgaactgcccaaagattctccgg
                                       M   M   N   C   P   K   I   L   R 190       200       210       220       230       240
cagttgggaagcaaagtgctgctgcccctgacatatgaaaggataaataagagcatgaac
 Q   L   G   S   K   V   L   L   P   L   T   Y   E   R   I   N   K   S   M   N
10

250       260       270       280       290       300
aaaagcatccacattgtcgtcacaatggcaaaatcactggagaacagtgtcgagaacaaa
 K   S   I   H   I   V   V   T   M   A   K   S   L   E   N   S   V   E   N   K
30

310       320       330       340       350       360
atagtgtctcttgatccatccgaagcaggccctccacgttatctaggagatcgctacaag
 I   V   S   L   D   P   S   E   A   G   P   P   R   Y   L   G   D   R   Y   K
50

370       380       390       400       410       420
ttttatctggagaatctcaccctggggatacgggaaagcaggaaggaggatgagggatgg
 F   Y   L   E   N   L   T   L   G   I   R   E   S   R   K   E   D   E   G   W
70

430       440       450       460       470       480
taccttatgaccctggagaaaaatgtttcagttcagcgcttttgcctgcagttgaggctt
 Y   L   M   T   L   E   K   N   V   S   V   Q   R   F   C   L   Q   R   L
90

490       500       510       520       530       540
tatgagcaggtctccactccagaaattaaagttttaaacaagacccaggagaacgggacc
 Y   E   Q   V   S   T   P   E   I   K   V   L   N   K   T   Q   E   N   G   T
110

550       560       570       580       590       600
tgcaccttgatactgggctgcacagtggagaaggggggaccatgtggcttacagctggagt
 C   T   L   I   L   G   C   T   V   E   K   G   D   H   V   A   Y   S   W   S
130
```

TABLE 1-continued

Human SLAM Sequences.

```
       610       620       630       640       650       660
gaaaaggcgggcacccacccactgaacccagccaacagctcccacctcctgtccctcacc
 E   K   A   G   T   H   P   L   N   P   A   N   S   S   H   L   L   S   L   T
150

670       680       690       700       710       720
ctcggccccagcatgctgacaatatctacatctgcaccgtgagcaaccctatcagcaac
 L   G   P   Q   H   A   D   N   I   Y   I   C   T   V   S   N   P   I   S   N
170

730       740       750       760       770       780
aattcccagaccttcagcccgtggcccggatgcaggacagacccctcagaaacaaaacca
 N   S   Q   T   F   S   P   W   P   G   C   R   T   D   P   S   E   T   K   P
190

790       800       810       820       830       840
tgggcagtgtatgctgggctgttaggggggtgtcatcatgattctcatcatggtggtaata
 W   A   V   Y   A   G   L   L   G   G   V   I   M   I   L   I   M   V   V   I
210

850       860       870       880       890       900
ctacagttgagaagaagaggtaaaacgaaccattaccagacaacagtggaaaaaaaaagc
 L   Q   L   R   R   R   G   K   T   N   H   Y   Q   T   T   V   E   K   K   S
230

910       920       930       940       950       960
cttacgatctatgcccaagtccagaaaccaggtcctcttcagaagaaacttgactccttc
 L   T   I   Y   A   Q   V   Q   K   P   G   P   L   Q   K   K   L   D   S   F 970       980       990       1000      1010      1020
ccagctcaggacccttgcaccaccatatatgttgctgccacagagcctgtcccagagtct
 P   A   Q   D   P   C   T   T   I   Y   V   A   A   T   E   P   V   P   E   S 1030      1040      1050      1060      1070      1080
gtccaggaaacaaattccatcacagtctatgctagtgtgacacttccagagagctgacac
 V   Q   E   T   N   S   I   T   V   Y   A   S   V   Y   L   P   E   S
```

The nucleotide and predicted amino acid sequence of mouse SLAM is shown in Table 2. One version of mouse SLAM is a type I transmembrane protein containing 9 potential N-linked glycosylation sites. The predicted unglycosylated MW is 40,000. The sequence shown is for mouse SLAM1 (in the plasmid pMSLAM1) which is the most abundant 1.8 kb SLAM cDNA, however, another 1.8 kb cDNA SLAM2 (in pMSLAM2), representing about 25% of the cDNA's was also isolated. SLAM2 shares about the first 1 kb of sequence with the SLAM1 sequence, but has different sequence at its 3' end. This SLAM2 cDNA in pMSLAM2 encodes a SLAM protein with a different cytoplasmic domain. The sequence of SLAM2 cDNA is shown in Table 2 and the position after which SLAM2 sequence varies from SLAM1 is indicated. Table 3 shows an alignment of selected human and mouse SLAM protein sequences. As is the case for human SLAM, mouse SLAM typically has one V and one C immunoglobulin domain and shares extensive amino-acid homology with human SLAM over the entire molecule, this being 88% counting conservative substitutions. The homology at the nucleotide level is about 70%. This mouse protein contains eight separate amino acid insertions relative to that human SLAM. The cysteines in the extracellular domain are all conserved and the context of three tyrosines in the cytoplasmic domain are perfectly retained. The two distal tyrosines in the cytoplasmic domain are not present in the alternatively spliced mouse SLAM2 molecule encoded by pSLAM2 (Table 2) and the unique portion of this cytoplasmic domain does not share high homology with human SLAM. There is an alternatively spliced form of human SLAM with a different cytoplasmic tail. The alternate sequence in pMSLAM2 is not homologous to the unique sequence of the human SLAM2 (pSURslam2), however, the position in the nucleotide sequence where the alternative exon is spliced is identical in both sequences (Table 2).

TABLE 2

Mouse SLAM sequences

Mouse SLAM1 (pMSLAM1) nucleotide and predicted amino acid sequence. Predicted leader sequences and the transmembrane sequence are underlined, though natural boundaries may be different, also depending upon cell type. Cysteines are found at amino acid residues numbered 32, 133, 161, 167, 212, 232, 276, and 310. Potential N-linked glycosylation sites are found at residues numbered 54, 58, 103, 126, 151, 158, 192, 210, and 226. Fragments between cysteines and/or N-linked glycosylation sites are particularly useful in generating antibodies. SEQ ID NO: 9 AND 10.

```
            10        20        30        40        50        60
       tcctgccgagctgagctgagctgagctcacagctgggaccctgtctgcgattgctggcta 70        80        90       100       110       120
       atggatcccaaaggatcccttcctggagaatacttctgtttctctccctggcttttgag
        M  D  P  K  G  S  L  S  W  R  I  L  L  F  L  S  L  A  F  E
        1

130       140       150       160       170       180
       ttgagctacggaacaggtggaggtgtgatggattgcccagtgattctccagaagctggga
        L  S  Y  G  T  G  G  G  V  M  D  C  P  V  I  L  Q  K  L  G
       21

190       200       210       220       230       240
       caggacacgtggctgcccctgacgaatgaacatcagataaataagagcgtgaacaaaagt
        Q  D  T  W  L  P  L  T  N  E  H  Q  I  N  K  S  V  N  K  S
       41

250       260       270       280       290       300
       gtccgcatcctcgtcaccatggcgacgtccccaggaagcaaatccaacaagaaaattgtg
        V  R  I  L  V  T  M  A  T  S  P  G  S  K  S  N  K  K  I  V
       61

310       320       330       340       350       360
       tcttttgatctctctaaagggagctatccagatcacctggaggatggctaccactttcaa
        S  F  D  L  S  K  G  S  Y  P  D  H  L  E  D  G  Y  H  F  Q
       81

370       380       390       400       410       420
       tcgaaaaacctgagcctgaagatcctcgggaacaggcgggagagtgaaggatggtacttg
        S  K  N  L  S  L  K  I  L  G  N  R  R  E  S  E  G  W  Y  L
       101

430       440       450       460       470       480
       gtgagcgtggaggagaacgtttctgttcagcaattctgcaagcagctgaagctttatgaa
        V  S  V  E  E  N  V  S  V  Q  Q  F  C  K  Q  L  K  L  Y  E
       121

490       500       510       520       530       540
       caggtctcccctccagagattaaagtgctaaacaaacccaggagaacgagaatgggacc
        Q  V  S  P  P  E  I  K  V  L  N  K  T  Q  E  N  E  N  G  T
       141

550       560       570       580       590       600
       tgcagcttgctgttggcctgcacagtgaagaaaggggaccatgtgacttacagctggagt
        C  S  L  L  L  A  C  T  V  K  K  G  D  H  V  T  Y  S  W  S
       161

610       620       630       640       650       660
       gatgaggcaggcacccacctgctgagccgagccaaccgctcccacctcctgcacatcact
        D  E  A  G  T  H  L  L  S  R  A  N  R  S  H  L  L  H  I  T
       181

670       690       690       700       710       720
       cttagcaaccagcatcaagacagcatctacaactgcaccgcaagcaaccctgtcagcagt
        L  S  N  Q  H  Q  D  S  I  Y  N  C  T  A  S  N  P  V  S  S
       201

730       740       750       760       770       780
       atctctaggaccttcaacctatcatcgcaagcatgcaagcaggaatcctcctcagaatcg
        I  S  R  T  F  N  L  S  S  Q  A  C  K  Q  E  S  S  S  E  S
       221

790       800       810       820       830       840
       agtccatggatgcaatatactcttgtaccactgggggtcgttataatcttcatcctggtt
        S  P  W  M  Q  Y  T  L  V  P  L  G  V  V  I  I  F  I  L  V
```

TABLE 2-continued

Mouse SLAM sequences

241

```
          850       860       870       880       890       900
ttcacggcaataataatgatgaaaagacaaggtaaatcaaatcactgccagccaccagtg
 F   T   A   I   I   M   M   K   R   Q   G   K   S   N   H   C   Q   P   P   V
261

910       920       930       940       950       960
gaagaaaaaagccttactatttatgcccaagtacagaaatcagggcctcaagagaagaaa
 E   E   K   S   L   T   I   Y   A   Q   V   Q   K   S   G   P   Q   E   K   K
281

970       980       990      1000      1010      1020
cttcatgatgccctaacagatcaggacccctgcacaaccatttatgtggctgccacagag
 L   H   D   A   L   T   D   Q   D   P   C   T   T   I   Y   V   A   A   T   E
301

1030      1040      1050      1060      1070      1080
cctgccccagagtctgtccaggaaccaaaccccaccacagtttatgccagtgtgacactg
 P   A   P   E   S   V   Q   E   P   N   P   T   T   V   Y   A   S   V   T   L
321

1090      1100      1110      1120      1130      1140
ccagagagctgacccatatacccagtgaaaggacttttttgaaggaggatagaagaaccaa
 P   E   S
341

1150      1160      1170      1180      1190      1200
aatccacactgaactggaccccggggtccaagttctctgtgacagaaactgcacatctgt
```

Mouse SLAM2 (pMSLAM2) nucleotide and predicted amino acid sequence. The point after which the sequence of mouse SLAM2 differ from mouse SLAM1 is indicated by • (nucleotide 944). SEQ ID NO: 11 and 12.

```
           10        20        30        40        50        60
tcctgccgagctgagctgagctgagctcacagctgggaccctgtctgcgattgctggcta 70        80        90       100       110       120
atggatcccaaaggatcccttcctggagaatacttctgtttctctccctggcttttgag
 M   D   P   K   G   S   L   S   W   R   I   L   L   F   L   S   L   A   F   E
 1

130       140       150       160       170       180
ttgagctacggaacaggtggaggtgtgatggattgcccagtgattctccagaagctggga
 L   S   Y   G   T   G   G   G   V   M   D   C   P   V   I   L   Q   K   L   G
21

190       200       210       220       230       240
caggacacgtggctgcccctgacgaatgaacatcagataaataagagcgtgaacaaaagt
 Q   D   T   W   L   P   L   T   N   E   H   Q   I   N   K   S   V   N   K   S
41

250       260       270       280       290       300
gtccgcatcctcgtcaccatggcgacgtccccaggaagcaaatccaacaagaaaattgtg
 V   R   I   L   V   T   M   A   T   S   P   G   S   K   S   N   K   K   I   V
61

310       320       330       340       350       360
tcttttgatctctctaaagggagctatccagatcacctggaggatggctaccactttcaa
 S   F   D   L   S   K   G   S   Y   P   D   H   L   E   D   G   Y   H   F   Q
81

370       380       390       400       410       420
tcgaaaaacctgagcctgaagatcctcgggaacaggcgggagagtgaaggatggtacttg
 S   K   N   L   S   L   K   I   L   G   N   R   R   E   S   E   G   W   Y   L
101

430       440       450       460       470       480
gtgagcgtggaggagaacgtttctgttcagcaattctgcaagcagctgaagctttatgaa
 V   S   V   E   E   N   V   S   V   Q   Q   F   C   K   Q   L   K   L   Y   E
121

490       500       510       520       530       540
caggtctcccctccagagattaaagtgctaaacaaacccaggagaacgagaatgggacc
 Q   V   S   P   P   E   I   K   V   L   N   K   T   Q   E   N   E   N   G   T
```

TABLE 2-continued

Mouse SLAM sequences

```
141
        550       560       570       580       590       600
tgcagcttgctgttggcctgcacagtgaagaaaggggaccatgtgacttacagctggagt
  C   S   L   L   L   A   C   T   V   K   K   G   D   H   V   T   Y   S   W   S
161
        610       620       630       640       650       660
gatgaggcaggcacccacctgctgagccgagccaaccgctcccacctcctgcacatcact
  D   E   A   G   T   H   L   L   S   R   A   N   R   S   H   L   L   H   I   T
181
        670       690       690       700       710       720
cttagcaaccagcatcaagacagcatctacaactgcaccgcaagcaaccctgtcagcagt
  L   S   N   Q   H   Q   D   S   I   Y   N   C   T   A   S   N   P   V   S   S
201
        730       740       750       760       770       780
atctctaggaccttcaacctatcatcgcaagcatgcaagcaggaatcctcctcagaatcg
  I   S   R   T   F   N   L   S   S   Q   A   C   K   Q   E   S   S   S   E   S
221
        790       800       810       820       830       840
agtccatggatgcaatatactcttgtaccactgggggtcgttataatcttcatcctggtt
  S   P   W   M   Q   Y   T   L   V   P   L   G   V   V   I   I   F   I   L   V
241
        850       860       870       880       890       900
ttcacggcaataataatgatgaaaagacaaggtaaatcaaatcactgccagccaccagtg
  F   T   A   I   I   M   M   K   R   Q   G   K   S   N   H   C   Q   P   P   V
261
        910       920       930       940       950       960
gaagaaaaaagccttactatttatgcccaagtacagaaatcaggggtacgttctatgcct
  E   E   K   S   L   T   I   Y   A   Q   V   Q   K   S   G   V   R   S   M   P
281
        970       980       990      1000      1010      1020
caccttgcgggagtgtctgtcatatttcgcacaggatttctgatagctgccttgcacaca
  H   L   A   G   V   S   V   I   F   R   T   G   F   L   I   A   A   L   H   T
301
       1030      1040      1050      1060      1070      1080
accatggtcctgcagggactcctagagtagatgaacttaagaaagcagaaaagtcaagaa
  T   M   V   L   Q   G   L   L   E
321
       1090      1100      1110      1120      1130      1140
caagagctcccccagtgtcactgacccttatattgtttgaacttgtagaaaacagtgaca
```

TABLE 3

Alignment of mouse SLAM1 to human SLAM1.

```
                              •
M   1'   MDPKGSLSWRILLFLSLAFELSYGTGGGVMDCPVILQKLGQDTWLPLTNEHQINKSVNKS
         ***** **  ..*******. ****** .*.** **..** .. **** *. ****.***
H   1"   MDPKGLLSLTFVLFLSLAFGASYGTGGRMMNCPKILRQLGSKVLLPLTYER-INKSMNKS

M   61'  VRILVTMATSPGSKSNKKIVSFDLSKGSYPDHLEDGYHFQSKNLSLKILGNRRESEGWYL
         ..*.****.*  ....  ..****.* *....  *  .*.* *.*   .**..*..*.*****
H   60"  IHIVVTMAKSLENSVENKIVSLDPSEAGPPRYLGDRYKFYLENLTLGIRESRKEDEGWYL
                              •                             •
M   121' VSVEENVSVQQFCKQLKLYEQVSPPEIKVLNKTQENENGTCSLLLACTVKKGDHVTYSWS
         ...*.*****.**.**.******.**********  *****.*.*.***.*****.****
H   120" MTLEKNVSVQRFCLQLRLYEQVSTPEIKVLNKTQ--ENGTCTLILGCTVEKGDHVAYSWS
                                       •
M   181' DEAGTHLLSRANRSHLLHITLSNQHQDSIYNCTASNPVSSISRTFNLSSQACKQESSSES
         ..****.*..**.**** .**..**.*.** **.***.*.  *.**.  ...*. . .**.
H   178" EKAGTHPLNPANSSHLLSLTLGPQHADNIYICTVSNPISNNSQTFS-PWPGCRTD-PSET

M   241' SPWMQYTLVPLGVVIIFILVFTAIIMMKRQGKSNHCQPPVEEKSLTIY̲AQVQKSGPQEKK
         .** *. .. **. **. **.....*. ...**.**.**.*...**.*********.** .**
```

TABLE 3-continued

Alignment of mouse SLAM1 to human SLAM1.

```
H  236"  KPWAVYAGL-LGGVIM-ILIMVVILQLRRRGKTNHYQTTVEKKSLTIYAQVQKPGPLQKK
                                                    •
M  301'  LHDALTDQDPCTTIYVAATEPAPESVQEPNPTTVYASVTLPES
         * *....**************.******.*..********
H  294"  L-DSFPAQDPCTTIYVAATEPVPESVQETNSITVYASVTLQRADTRDQQRDFLKENGKTK
```

• indicates a conserved cysteine;
* indicates identical amino acids;
. indicates a conserved amino acid;
conserved cysteines in the cytoplasmic domain are underlined.

Some homology is apparent in the extracellular domains of human SLAM with mouse 2B4, human CD48, and human LFA-3 (CD58) protein sequences. Alignment of the sequences reveals portions of shared homology, disparate homology, common motifs, and partly shared features.

The natural antigens are capable of mediating various biochemical responses which lead to biological or physiological responses in target cells. The best characterized embodiment was initially described in human, but human and mouse variants are also described herein. Additional sequences for proteins in other mammalian species, e.g., primates and rodents, should also be available. See below. The descriptions below are directed, for exemplary purposes, to a human SLAM, but are likewise applicable to related embodiments from other species.

Isolated human SLAM protein is a protein which exhibits structural features characteristic of a cell surface antigen. The protein is easily detected on particular cell types, others express lesser amounts. See Table 4. The SLAM mediates a biochemical response to binding of an antibody, or other yet unidentified ligands, leading to signal transduction and cellular response. In particular, the SLAM antigen has been isolated by expression cloning using a specific antibody. The SLAM antigen was isolated and characterized as a protein which migrates on polyacrylamide gel electrophoresis with a mobility characteristic of a protein of about 70 kD. The core protein, after treatment with N-glycanase, has a mobility of about a 40 kd protein.

TABLE 4

Cellular expression of SLAM. RNA from various cells and tissues was subject to reverse transcription and PCR using SLAM specific primers. Rough qualitative determinations are provided, though a negative merely means below threshold detection levels. Thymus also expresses the message.

| cell type | expression |
|---|---|
| JY EBV transformed B cells | + |
| purified B cells CD20+ | + |
| CD4+ T-cell clone S11 | + |
| CD4+ T-cell clone S40 | + |
| CD4+ T-cell clone B21 | + |
| CD4+ T-cell clone B21 activated | + |
| purified NK cells | + |
| purified NK cells | + |
| fetal liver | − |
| fetal bone marrow | − |
| fetal thymus | + |
| small intestine | − |
| brain | − |
| kidney | − |
| heart | − |
| FL508 pre-T cell line | + |
| TN92 pre-T cell line | + |

The SLAM antigen should be present in the identified tissue types and the interaction of the antigen with its binding partner should be important for mediating various aspects of cellular physiology or development.

II. Purified SLAM

Human and mouse SLAM amino acid sequences are shown in SEQ ID NO: 2, 4, 6, 8, 10, and 12. These amino acid sequences, provided amino to carboxy, are important in providing sequence information in the antigen allowing for distinguishing the protein from other proteins and exemplifying numerous variants. Moreover, the peptide sequences allow preparation of peptides to generate antibodies to recognize such segments, and allow preparation of oligonucleotide probes, both of which are strategies for detection or isolation, e.g., cloning, of genes encoding such sequences.

As used herein, the term "human SLAM" shall encompass, when used in a protein context, a protein having amino acid sequences shown in SEQ ID NO: 2, 4, 6, or 8, or a significant fragment of such a protein, or another highly homologous protein derived from human. Clearly, there are mRNA species representing splicing variants. It also refers to a human derived polypeptide which exhibits similar biological function or interacts with SLAM specific binding components. These binding components, e.g., antibodies, typically bind to a SLAM with high affinity, e.g., at least about 100 nM, usually better than about 30 nM, preferably better than about 10 nM, and more preferably at better than about 3 nM. Homologous proteins would be found in mammalian species other than human, e.g., primates or rodents. Non-mammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids.

The term "binding composition" refers to molecules that bind with specificity to SLAM, e.g., in a cell adhesion pairing type fashion, or an antibody-antigen interaction. It also includes compounds, e.g., proteins, which specifically associate with SLAM, including in a natural physiologically relevant protein-protein interaction, either covalent or non-covalent. The molecule may be a polymer, or chemical reagent. A functional analog may be an antigen with structural modifications, or it may be a molecule which has a molecular shape which interacts with the appropriate binding determinants. The compounds may serve as agonists or antagonists of the binding interaction, see, e.g., Goodman, et al. (eds.) (1990) *Goodman & Gilman's: The Pharmacological Bases of Therapeutics* (8th ed.), Pergamon Press.

Substantially pure typically means that the protein is free from other contaminating proteins, nucleic acids, or other biologicals derived from the original source organism.

Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein.

III. Physical Variants

This invention also encompasses proteins or peptides having substantial amino acid sequence identity with the amino acid sequence of the SLAM. The variants include species or allelic variants.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps, Strina Edits, and Macromolecules: The Theory and Practice of Seauence Comparison*, Addison-Wesley, Reading, Mass.; and software packages from IntelliGenetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% identity (if gaps can be introduced), to 50–100% identity (if conservative substitutions are included) with the amino acid sequence of the SLAM. Identity measures will be at least about 35%, generally at least about 40%, often at least about 50%, typically at least about 60%, usually at least about 70%, preferably at least about 80%, and more preferably at least about 90%.

The isolated SLAM DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant SLAM" encompasses a polypeptide otherwise falling within the sequence identity definition of the SLAM as set forth above, but having an amino acid sequence which differs from that of SLAM as normally found in nature, whether by way of deletion, substitution, or insertion. This generally includes proteins having significant identity with a protein having sequences of SEQ ID NO: 2, 4, 6, 8, 10, or 12, and as sharing various biological activities, e.g., antigenic or immunogenic, with those sequences, and in preferred embodiments contain most of the full length disclosed sequences. Full length sequences will typically be preferred, though truncated versions will also be useful. Similar concepts apply to different SLAM proteins, particularly those found in various warm blooded animals, e.g., mammals and birds. These descriptions are generally meant to encompass all SLAM proteins, not limited to the particular human or mouse embodiments specifically discussed.

SLAM mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Methods in Enzymol.* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to SLAMs may result from the inhibition of binding of the antigen to its binding partner, e.g., another of itself, likely through competitive inhibition. Thus, in vitro assays of the present invention will often use isolated protein, membranes from cells expressing a membrane associated recombinant SLAM, soluble fragments comprising antigen binding segments of these proteins, or fragments attached to solid phase substrates. These assays will also allow for the diagnostic determination of the effects of either binding segment mutations and modifications, or antigen mutations and modifications, e.g., SLAM analogs.

This invention also contemplates the use of competitive drug screening assays, e.g., where neutralizing antibodies to antigen or binding fragments compete with a test compound for binding to the protein. "Derivatives" of SLAM antigens include amino acid sequence mutants, glycosylation variants, and covalent or aggregate conjugates with other chemical moieties. Covalent derivatives can be prepared by linkage of functionalities to groups which are found in SLAM amino acid side chains or at the N- or C-termini, e.g., by standard means. See, e.g., Lundblad and Noyes (1988) *Chemical Reagents for Protein Modification,* vols. 1–2, CRC Press, Inc., Boca Raton, Fla.; Hugli (ed.) (1989) *Techniques in Protein Chemistry,* Academic Press, San Diego, Calif.; and Wong (1991) *Chemistry of Protein Conjugation and Cross Linking,* CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between SLAMs and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence or His6 sequence. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology,* Greene and Wiley, NY. Techniques for synthesis of polypeptides are described, e.g., in Merrifield (1963) *J. Amer. Chem. Soc.* 85:2149–2156; Merrifield (1986) *Science* 232: 341–347; Atherton, et al. (1989) *Solid Phase Peptide Synthesis: A Practical Aporoach,* IRL Press, Oxford; and Grant (1992) *Synthetic Peptides: A User's Guide,* W. H. Freeman, NY.

This invention also contemplates the use of derivatives of SLAMs other than variations in amino acid sequence or glycosylation. Such derivatives may involve covalent or aggregative association with chemical moieties. Covalent or aggregative derivatives will be useful as immunogens, as reagents in immunoassays, or in purification methods such as for affinity purification of binding partners, e.g., other antigens. A SLAM can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-SLAM antibodies or an alternative binding composition. The SLAMs can also be labeled with a detectable group, e.g., for use in diagnostic assays. Purification of SLAM may be effected by an immobilized antibody or complementary binding partner.

A solubilized SLAM or fragment of this invention can be used as an immunogen for the production of antisera or antibodies specific for binding to the antigen or fragments thereof. Purified antigen can be used to screen monoclonal antibodies or antigen-binding fragments, encompassing antigen binding fragments of natural antibodies. Purified SLAMs can also be used as a reagent to detect antibodies generated in response to the presence of elevated levels of the antigen or cell fragments containing the antigen, both of which may be diagnostic of an abnormal or specific physiological or disease condition. This invention contemplates antibodies raised against amino acid sequences encoded by nucleotide sequences shown in SEQ ID NO: 1, 3, 5, 7, 9, or 11, or fragments of proteins containing them. In particular, this invention contemplates antibodies having binding affinity to or being raised against specific fragments which are predicted to lie outside of the lipid bilayer, both extracellular or intracellular.

The present invention contemplates the isolation of additional closely related species variants. Southern and Northern blot analysis should establish that similar genetic entities exist in other mammals. It is likely that SLAMs are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species variants of them. In particular, the present invention provides useful probes for identifying additional homologous genetic entities in different species.

The isolated genes will allow transformation of cells lacking expression of a corresponding SLAM, e.g., either species types or cells which lack corresponding antigens and exhibit negative background activity. This should allow analysis of the function of SLAM in comparison to untransformed control cells.

Dissection of critical structural elements which effect the various activation or differentiation functions mediated through these antigens is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

Intracellular functions would probably involve segments of the antigen which are normally accessible to the cytosol. However, protein internalization may occur under certain circumstances, and interaction between intracellular components and "extracellular" segments may occur. The specific segments of interaction of SLAM with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of SLAM will be pursued. The controlling elements associated with the antigens should exhibit differential physiological, developmental, tissue specific, or other expression patterns. Upstream or downstream genetic regions, e.g., control elements, are of interest. In particular, physiological or developmental variants, e.g., multiple alternatively processed forms of the antigen have been found. See, e.g., SEQ ID NO: 1 and 3. Thus, differential splicing of message may lead to an assortment of membrane bound forms, soluble forms, and modified versions of antigen.

Structural studies of the antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various SLAMs, including species or allelic variants, and fragments thereof, both in their naturally occurring forms and in their recombinant forms. Additionally, antibodies can be raised to SLAMs in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective SLAMs, or screened for agonistic or antagonistic activity, e.g., mediated through the antigen or its binding partner. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying SLAM protein or its binding partners. See, e.g., Chan (ed.) (1987) *Immunology: A Practical Guide*, Academic Press, Orlando, Fla.; Price and Newman (eds.) (1991) *Principles and Practice of Immunoassay*, Stockton Press, N.Y.; and Ngo (ed.) (1988) *Nonisotopic Immunoassay*, Plenum Press, N.Y. Cross absorptions or other tests will identify antibodies which exhibit various spectra of specificities, e.g., unique or shared species specificities.

Further, the antibodies, including antigen binding fragments, of this invention can be potent antagonists that bind to the antigen and inhibit functional binding or inhibit the ability of a binding partner to elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology,* Hoeber Medical Division, Harper and Row, 1969; Landsteiner (1962) *Specificity of Serological Reactions,* Dover Publications, New York; Williams, et al. (1967) *Methods in Immunology and Immunochemistry,* vol. 1, Academic Press, New York; and Harlow and Lane (1988) *Antibodies: A Laboratory Manual,* CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.), Academic Press, New York; and particularly in Kohler and Milstein (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemi-luminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3–55.

Antibodies raised against each SLAM will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding SLAM, e.g., from a natural source. Typically, it will be useful in isolating a gene from mammal, and similar procedures will be applied to isolate genes from other species, e.g., warm blooded animals, such as birds and mammals. Cross hybridization will allow isolation of SLAM from other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual,* Cold Spring Harbor Press. Alternatively, the SLAM can be used as a specific binding reagent, and advantage can be taken of its specificity of binding, much like an antibody would be used.

For example, the specific binding composition could be used for screening of an expression library made from a cell line which expresses a SLAM. The screening can be standard staining of surface expressed antigen, or by panning. Screening of intracellular expression can also be performed by various staining or immunofluorescence procedures. The binding compositions could be used to affinity purify or sort out cells expressing the protein.

The peptide segments can also be used to predict appropriate oligonucleotides to screen a library. The genetic code can be used to select appropriate oligonucleotides useful as probes for screening. See, e.g., SEQ ID NO: 1 or 3. In combination with polymerase chain reaction (PCR) techniques, synthetic oligonucleotides will be useful in selecting correct clones from a library. Complementary sequences will also be used as probes, primers, or antisense strands. Based upon identification of the likely extracellular domain, various fragments should be particularly useful, e.g., coupled with anchored vector or poly-A complementary PCR techniques or with complementary DNA of other peptides.

This invention contemplates use of isolated DNA or fragments to encode a biologically active corresponding SLAM polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact antigen, or fragment, and have an amino acid sequence disclosed in, e.g., SEQ ID NO: 1 or 3. Further, this invention covers the use of isolated or recombinant DNA, or fragments thereof, which encode proteins which are homologous to a SLAM or which was isolated using cDNA encoding a SLAM as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides.

A DNA which codes for a SLAM protein will be particularly useful to identify genes, mRNA, and cDNA species which code for related or homologous proteins, as well as DNAs which code for homologous proteins from different species. There are likely homologues in other species, including primates, rodents, and birds. Various SLAM proteins should be homologous and are encompassed herein. However, even proteins that have a more distant evolutionary relationship to the antigen can readily be isolated under appropriate conditions using these sequences if they are sufficiently homologous. Primate SLAM proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology,* Academic Press, San Diego, pp. 1502–1504; Travis (1992) *Science* 256:1392–1394; Kuhn, et al. (1991) Science 254:707–710; Capecchi (1989) *Science* 244:1288; Robertson (1987)(ed.) *Teratocarcinomas and Embryonic Stem Cells: A Practical Approach,* IRL Press, Oxford; and Rosenberg (1992) *J. Clinical Oncology* 10:180–199.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of SLAM, e.g., in SEQ ID NO: 1, 3, 5, 7, 9, or 11. Typically, selective hybridization will occur when there is at least about 55% homology over a stretch of at least about 30 nucleotides, preferably at least about 75% over a stretch of about 25 nucleotides, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., preferably in excess of about 70° C. Stringent salt conditions will ordinarily be less than about 1000 mM, usually less than about 400 mM, typically less than about 250 mM, preferably less than about 150 mM. However, the combination of parameters is much more important than the measure of any single parameter. See, e.g., Wetmur and Davidson (1968) *J. Mol. Biol.* 31:349–370.

SLAM from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making SLAM; Mimetics

DNA which encodes the SLAM or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed.) (1984) *DNA Cloning: A Practical Approach,* IRL Press, Oxford. Alternatively, the sequences provided herein provide useful PCR primers or allow synthetic or other preparation of suitable genes encoding a SLAM.

This DNA can be expressed in a wide variety of host cells for the synthesis of a full-length SLAM or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Clonina Vectors: A Laboratory Manual,* Elsevier, N.Y.; and Rodriguez, et al. (1988)(eds.) *Vectors: A Survey of Molecular Cloning Vectors and Their Uses,* Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See e.g., Rodriguez, et al., Chapter 10, pp. 205–236; Balbas and Bolivar (1990) *Methods in Enzymology* 185:14–37; and Ausubel, et al. (1993) *Current Protocols in Molecular Biology,* Greene and Wiley, NY.

Representative examples of suitable expression vectors include pCDNA1; pCD, see Okayama, et al. (1985) *Mol. Cell Biol.* 5:1136–1142; pMClneo Poly-A, see Thomas, et al. (1987) *Cell* 51:503–512; and a baculovirus vector such as pAC 373 or pAC 610. See, e.g., Miller (1988) *Ann. Rev. Microbiol.* 42:177–199.

It will often be desired to express a SLAM polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The SLAM, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the SLAM has been characterized, fragments or derivatives thereof can be prepared by conventional processes for synthesizing peptides. These include processes such as are described in Stewart and Young (1984) *Solid Phase Peptide Synthesis,* Pierce Chemical Co., Rockford, Ill.; Bodanszky and Bodanszky (1984) *The Practice of Peptide Synthesis,* Springer-Verlag, New York; Bodanszky (1984) *The Principles of Peptide Synthesis,* Springer-Verlag, New York; and Villafranca (ed.) (1991) *Techniques in Protein Chemistry II,* Academic Press, San Diego, Calif.

VIII. Uses

The present invention provides reagents which will find use in diagnostic applications as described elsewhere herein, e.g., in the general description for T cell mediated conditions, or below in the description of kits for diagnosis.

This invention also provides reagents with significant therapeutic value. The SLAM (naturally occurring or recombinant), fragments thereof, and antibodies thereto, along with compounds identified as having binding affinity to SLAM, should be useful in the treatment of conditions associated with abnormal physiology or development, including abnormal proliferation, e.g., cancerous conditions, or degenerative conditions. In particular, modulation of development of lymphoid cells will be achieved by appropriate therapeutic treatment using the compositions provided herein. For example, a disease or disorder associated with abnormal expression or abnormal signaling by a SLAM should be a likely target for an agonist or antagonist of the antigen. The antigen plays a role in regulation or development of hematopoietic cells, e.g., lymphoid cells, which affect immunological responses, e.g., autoimmune disorders.

In particular, the antigen has been demonstrated to provide a costimulatory signal to T cell activation. Thus, the SLAM has a role in T cell to T cell interactions. These interactions lead, in particular contexts, to cell proliferation, enhanced cytokine synthesis by the cells, and consequential amplification of T cell proliferation.

Moreover, the SLAM induced production of interferon-γ suggests that certain agonists to SLAM could direct T cell responses towards a Th0/Th1 pathway, and thus suppress a Th2 type response. Among these agonists should be various antibodies which recognize the appropriate epitopes, e.g., which mimic binding of SLAM to its ligand.

Conversely, antagonists of SLAM, such as the naturally occurring secreted form of SLAM or blocking antibodies, may provide a selective and powerful way to block immune responses in abnormal situations, e.g., autoimmune disorders, including rheumatoid arthritis, systemic lupus erythematosis (SLE), Hashimoto's autoimmune thyroiditis, as well as acute and chronic inflammatory responses in which T cell activation, expansion, and/or immunological T cell memory play an important role. See also Samter, et al. (eds) *Immunological Diseases* vols. 1 and 2, Little, Brown and Co. Suppression of T cell activation, expansion, and/or cytokine release by the naturally occurring secreted form of SLAM, which can be produced in large quantities by recombinant methods, or by blocking antibodies, should be effective in many disorders in which abnormal T cell responses are of importance.

The SLAM appears to be coexpressed with CD45RO, which is a marker for primed, or memory, T cells. SLAM is also absent in the CD45RA cells, which represent the naive T cell subset. As such, the SLAM can also serve as a diagnostic marker for memory T cells.

Various abnormal conditions are known in each of the cell types shown to possess SLAM MRNA by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine*, Oxford University Press, Oxford. Many other medical conditions and diseases involve T cells or are T cell mediated, and many of these will be responsive to treatment by an agonist or antagonist provided herein. See, e.g., Stites and Terr (eds; 1991) *Basic and Clinical Immunology* Appleton and Lange, Norwalk, Conn.; and Samter, et al. (eds) *Immunological Diseases* Little, Brown and Co. These problems should be susceptible to prevention or treatment using compositions provided herein.

SLAM antibodies can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using SLAM or fragments thereof can be performed to identify compounds having binding affinity to or other relevant biological effects on SLAM functions, including isolation of associated components. Subsequent biological assays can then be utilized to determine if the compound has intrinsic stimulating activity and is therefore a blocker or antagonist in that it blocks the activity of the antigen. Likewise, a compound having intrinsic stimulating activity can activate the signal pathway and is thus an agonist in that it simulates the activity of SLAM. This invention further contemplates the therapeutic use of blocking antibodies to SLAM as antagonists and of stimulatory antibodies, e.g., A12, as agonists. This approach should be particularly useful with other SLAM species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous or long term administration. See, e.g., Langer (1990) *Science* 249:1527–1533.

SLAM, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds.) (1993) *Pharmaceutical Dosage Forms: Parenteral Medications*, Dekker, N.Y.; Lieberman, et al. (eds.) (1990) *Pharmaceutical Dosage Forms: Tablets*, Dekker, N.Y.; and Lieberman, et al. (eds.) (1990) *Pharmaceutical Dosage Forms: Disoerse Systems*, Dekker, N.Y. The therapy of this invention may be combined with or used in association with other agents.

Both the naturally occurring and the recombinant form of the SLAMs of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble SLAM as provided by this invention.

Other methods can be used to determine the critical residues in the SLAM-SLAM interactions. Mutational analysis can be performed, e.g., see Somoza, et al. (1993) *J. Exptl. Med.* 178:549–558, to determine specific residues critical in the interaction and/or signaling. Both extracellular domains, involved in the homophilic interaction, or an intracellular domain, which provides interactions important in intracellular signaling, will be useful.

For example, antagonists can normally be found once the antigen has been structurally defined, e.g., by tertiary structure data. Testing of potential interacting analogs is now possible upon the development of highly automated assay methods using a purified SLAM. In particular, new agonists and antagonists will be discovered by using screening techniques described herein of particular importance are compounds found to have a combined binding affinity for a spectrum of SLAM molecules, e.g., compounds which can serve as antagonists for species variants of SLAM.

One method of drug screening utilizes eukaryotic or prokaryotic host cells which are stably transformed with recombinant DNA molecules expressing a SLAM. Cells may be isolated which express a SLAM in isolation from other molecules. Such cells, either in viable or fixed form, can be used for standard binding partner binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Another technique for drug screening involves an approach which provides high throughput screening for compounds having suitable binding affinity to a SLAM and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified SLAM, and washed. The next step involves detecting bound SLAM.

Rational drug design may also be based upon structural studies of the molecular shapes of the SLAM and other effectors or analogs. Effectors may be other proteins which mediate other functions in response to binding, or other proteins which normally interact with SLAM. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography,* Academic Press, New York.

IX. Kits

This invention also contemplates use of SLAM proteins, fragments thereof, peptides, and their fusion products in a variety of diagnostic kits and methods for detecting the presence of another SLAM or binding partner. Typically the kit will have a compartment containing either a defined SLAM peptide or gene segment or a reagent which recognizes one or the other, e.g., SLAM fragments or antibodies.

A kit for determining the binding affinity of a test compound to a SLAM would typically comprise a test compound; a labeled compound, for example a binding partner or antibody having known binding affinity for SLAM; a source of SLAM (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the SLAM signaling pathway. The availability of recombinant SLAM polypeptides also provide well defined standards for calibrating such assays.

A preferred kit for determining the concentration of, e.g., a SLAM in a sample would typically comprise a labeled compound, e.g., binding partner or antibody, having known binding affinity for the antigen, a source of antigen (naturally occurring or recombinant) and a means for separating the bound from free labeled compound, e.g., a solid phase for immobilizing the SLAM. Compartments containing reagents, and instructions, will normally be provided.

Antibodies, including antigen binding fragments, specific for the SLAM or fragments are useful in diagnostic applications to detect the presence of elevated levels of SLAM and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual,* CSH Press, NY; and Coligan, et al. (eds.) (1993) *Current Protocols in Immunology,* Greene and Wiley, NY.

Anti-idiotypic antibodies may have similar use to diagnose presence of antibodies against a SLAM, as such may be diagnostic of various abnormal states. For example, overproduction of SLAM may result in production of various immunological reactions which may be diagnostic of abnormal physiological states, particularly in proliferative cell conditions such as cancer or abnormal activation or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled SLAM is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the binding partner, test compound, SLAM, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free SLAM, or alternatively the bound from the free test compound. The SLAM can be immobilized on various matrixes followed by washing. Suitable matrixes include plastic such as an ELISA plate, filters, and beads. See, e.g., Coligan, et al. (eds.) (1993) *Current Protocols in Immunology*, Vol. 1, Chapter 2, Greene and Wiley, N.Y. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a SLAM. These sequences can be used as probes for detecting levels of the SLAM message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci.* 79:4381–4385; Caskey (1987) *Science* 236:962–967; and Wilchek et al. (1988) *Anal. Biochem.* 171:1–32.

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

The binding of SLAM-Ig to SLAM transfected L cells demonstrates that SLAM can interact with itself as a ligand. Native gel electrophoresis of purified SLAM-Ig indicated directly, with the existence of high molecular weight forms, that SLAM-Ig molecules were also capable of homophilic interaction in solution. Although monomeric and dimeric forms of SLAM-Ig were predominant on the native gel they were not distinct bands, indicative of a fairly weak molecular interaction susceptible to dissociation during electrophoresis. Indeed the level of SLAM-Ig binding to SLAM expressing L cells was lower than that observed using an equivalent concentration of monoclonal antibody, suggesting that SLAM-SLAM interaction is weaker than the interaction of the mAb A12 with SLAM. Interactions between other Ig superfamily members are substantially weaker than the interaction of antibodies (van der Merwe and Barclay (1994) *TIBS* 19:354–358). Consistent with SLAM being a ligand for itself, SLAM-Ig binding was observed on T-cell clones and EBV-transformed B cells, both cell types which express significant levels of SLAM. The levels of SLAM on CD45RO$^+$ T cells from PBMC correlated with SLAM-Ig binding levels following activation. These data do not exclude that there may be another ligand for SLAM, but there is no evidence for another ligand since no SLAM-negative cell-type tested so far has shown SLAM-Ig binding, and when SLAM-Ig binding was observed it was proportional to the level of SLAM expression.

Consistent with the biochemical evidence that SLAM is a natural ligand for itself, L cells transfected with SLAM could provide a direct co-stimulatory signal for CD4$^+$ T-cell clones. Engagement of SLAM with the mAb A12 provides a significant co-stimulatory signal for T-cell activation. As observed with the agonistic mAb A12, activation of CD4$^+$ T-cell clones via SLAM expressed on L cells, in combination with anti-CD3, leads to large increases in proliferation. Co-stimulation of proliferation with suboptimal doses of anti-CD3 was observed with SLAM-transfectants. The stimulation provided by SLAM transfected L cells was substantial enough to lead directly to T-cell proliferation in the absence of other stimuli. In this respect, the direct stimulatory signal provided by SLAM expressed on L cells is unique, and is not observed even for the classical co-stimulatory molecules B7 (Jenkins and Johnson (1993) *Curr. Opin. Immunol.* 5:361–367) and B70 (Azuma, et al. (1993) *Nature* 366:76–79).

The ligand for B7 is CD28, and anti-CD28 mAbs do not directly stimulate proliferation of T-cell clones. However, the anti-SLAM mAb A12, or its F(ab)$_2$ fragments can directly induce T-cell proliferation. The consequences of engagement of SLAM on T-cell clones by SLAM on transfected L cells, or by mAb A12 or its F(ab)$_2$ fragments are concordant. Thus, direct engagement of SLAM, without the involvement of other molecules in the interaction, is sufficient to induce the functional effects observed. This does not preclude the likely interaction of SLAM with signal-transducing molecules, or diminish the importance of other cell-surface molecule interactions in achieving the most potent functional effects of SLAM engagement, such as the tremendous co-stimulatory effects via SLAM on T cells stimulated in an antigen-specific manner.

The SLAM gene was localized to the interface of bands q21.3 and q22 on human chromosome 1. This region of chromosome 1 appears to be an important locus for genes involved in cell-cell interactions. The genes for selectins (Watson, et al. (1990) *J. Exp. Med.* 172:263–272), molecules involved in leukocyte adhesion and trafficking, also localize to lq22–23. Another gene at this locus (lq21.3–23) is the gene for myelin Po (Pham-Dinh, et al. (1993) *Hum. Mol. Genet.* 2:2051–2054), the most abundant protein in myelin (Filbin, et al. (1990) *Nature* 344:871–872). Like SLAM, myelin Po is a member of the Ig-superfamily (Williams and Barclay (1988) *Annu. Rev. Immunol.* 6:381–405) and also interacts homophilically. Normal myelin structure relies upon the self-interaction of myelin Po, and inherited mutations in myelin Po are responsible for the Charcot-Marie-Tooth neuropathy, type lb (Kulkens, et al. (1993) *Nat. Genet.* 5:35–39; Hayasaka, et al. (1993) *Nat. Genet.* 5:31–34). Many members of the Ig-superfamily interact heterophilically with related family members, prominent examples being CD2 with LFA-3 (Selvaraj, et al. (1987) *Nature* 326:400–403) or CD48 (van der Merwe, et al. (1993) *EMBO J.* 12:4945–4954); CD28 with B7-1 (Linsley, et al. (1990)

*Proc. Natl. Acad. Sci. USA* 87:5031–5035) or B7-2 (Freeman, et al. (1993) *Science* 262:909–911; Azuma, et al. (1993) *Nature* 366:76–79); and the TCR with MHC class II (Matsui, et al. (1991) *Science* 254:1788–1791). That many Ig-superfamily members can interact in this way may be the result of evolution after gene duplication of a homophilically interacting precursor (Williams and Barclay (1988) *Annu. Rev. Immunol.* 6:381–405). SLAM and myelin Po may have retained a primordial function of Ig-superfamily members to interact homophilically.

The gene for CD48 localizes to the same part of chromosome 1 as SLAM at lq21–23 (Staunton, et al. (1989) *J. Exp. Med.* 169:1087–1099). CD48, reported to be a weak ligand for CD2 (van der Merwe, et al. (1993) *EMBO J.* 12:4945–4954), and 2B4, a signaling molecule expressed on murine NK cells and cytotoxic T cells (Mathew, et al. (1993) *J. Immunol.* 151:5328–5337) for which a ligand has not been reported, are the most closely related molecules to SLAM. Interestingly, SLAM, CD48, and 2B4 all have one V and one C domain and can be distinguished from other members of the Ig-superfamily by the conservation of the sequence CXLXLXC, the second cysteine being the tether for the C-domain and the first cysteine a conserved residue probably between the V- and C-domains. CD48 and 2B4 have not yet been directly assessed for their ability to interact homophilically, however it has been reported that a recombinant soluble form CD48 tends to aggregate in solution. The relatedness and chromosomal co-localization of CD48 and SLAM is indicative of evolutionary divergence following gene duplication.

Other large Ig-superfamily members with multiple domains have been reported to interact homophilically, and these include platelet-endothelial cell adhesion molecule (CD31) (Watt, et al. (1993) *Blood* 82:2649–2663), neuron-glia cell adhesion molecule (Grumet and Edelman (1988) *J. Cell Biol.* 106:487–503), neuron-glia-related cell adhesion molecule (Mauro, et al. (1992) *J. Cell Biol.* 119:191–202), neural cell adhesion molecule or CD56 (Rao, et al. (1992) *J. Cell Biol.* 118:937–949), and the carcinoembryonic antigen (Zhou, et al. (1993) *J. Cell Biol.* 122:951–960).

An alternatively spliced form of SLAM lacking a 90 bp exon, corresponding to and precisely encompassing the transmembrane region of SLAM encodes a secreted form of SLAM. This naturally produced molecule expressed by activated T cells may suppress T-cell function and may be part of a negative feedback loop to attenuate, or locally restrict SLAM mediated activation upon cell-cell interaction. SLAM mediated T-cell activation is resistant to cyclosporin, consistent with the inability of anti-IL-2 antibodies to inhibit SLAM induced T-cell clone proliferation. Given the potent co-stimulatory effects of SLAM engagement on T-cell proliferation and Th1 cytokine production, the potential immunosuppressive activity of soluble SLAM may make it an effective adjunct for inhibiting ongoing immune responses relatively resistant to cyclosporin such as that seen in allograft rejection (Pereira, et al. (1990) *J. Immunol.* 144:2109–2116; Zeevi, et al. (1988) *Hum. Immunol.* 21:143–153).

SLAM engagement has unique consequences for T-cell activation in terms of its ability to modulate cytokine production profiles toward a Th0/Th1 subtype and, under some circumstances, to directly induce T-cell proliferation. The newly described SLAM appears to be a member of the Ig-superfamily in addition to the TCR, CD28, CTLA-4, CD4, and CD2, and its engagement regulates T-cell responses. The presence of SLAM on lymphocytes indicates that activated lymphocytes themselves can provide a significant co-stimulus. This is not unexpected, as the most predominant cell type in lymphoid organs are lymphocytes, which are statistically ever present collaborators, and the major source of autocrine T-cell growth factors such as IL-2. SLAM may not only provide strong co-stimulatory signals, but could also be involved in maintaining the relative segregation and lymphocyte accumulation within lymphoid organs. Most work on T-cell co-stimulation has focused on different antigen-presenting cells and the molecules they express, particularly B7 and B70, the ligands for CD28 and CTLA-4 (Jenkins (1994) *Immunity* 1:443–446). B cells are an antigen-presenting cell which when activated express SLAM, which may support B-T cell collaboration leading to Ig production. Consistent with the co-stimulatory functions described herein for SLAM, recent studies on CD28 deficient mice have invoked a role for other co-stimulatory molecules in T cell activation (Green, et al. (1994) *Immunity* 1:501–508; Shahinian, et al. (1993) *Science* 261:609–612) and have indicated that co-stimulation provided by other T cells can contribute to T cell activation (Green, et al. (1994) *Immunity* 1:501–508; Jenkins (1994) *Immunity* 1:443–446) In addition to SLAM, activated human T cells do express MHC class II and B7 and have been shown to be able to present antigen (Azuma, et al. (1993) *J. Exp. Med.* 177:845–850), emphasizing the potential of interactions between T cells, which may alleviate the requirement for the constant presence of antigen-presenting cells during the clonal expansion of T cells. Naturally produced soluble SLAM should provide a useful antagonist to further assess the importance of SLAM-SLAM interactions in the development of human immune reactions.

Anti-SLAM monoclonal antibodies inhibit IL-4 induced IgE synthesis, which indicates that signaling through SLAM either at the T helper cell or at the B cell levels, inhibits productive T-B cell interaction, which result in IL-4 driven IgE switching and IgE production. This effect can be direct, e.g., through interactions between SLAM on T cells and SLAM on B cells, or indirect, e.g., by inducing cytokine production by the T-helper cell, which inhibits IL-4 driven IgE synthesis. Interferon-$\gamma$ is the primary example of such a cytokine.

These results also suggest that soluble forms of SLAM with agonist activities may be able to prevent IL-4 and/or IL-13 driven IgE synthesis in atopic patients, and thereby will have therapeutic utility in downregulating IgE-mediated allergic diseases. In addition, the fact that engagement of SLAM induces preferentially Th1 cytokine production, SLAM agonists may have general clinical utility in redirecting Th2 responses to Th1 responses in diseases in which a clear Th2 profile has been implicated, such as allergy, certain autoimmune diseases, or certain inflammatory diseases. This includes Hashimoto's thyroiditis.

On the other hand, SLAM antagonists will have an opposite effect; that is, blocking of Th1 responses in the disease situations caused by Th1 cells and Th1 cell derived cytokines, such as infectious diseases, including, e.g., tuberculosis and leprosy, or autoimmune diseases, e.g., rheumatoid arthritis and autoimmune uveitis.

These therapeutic reagents will be useful also in modulating such responses as to parasitic infections, to modulate a vaccine reaction, or in Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual* (2d ed.), vols 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene and Wiley, New York; Innis, et al. (eds.) (1990) *PCR Protocols: A Guide to Methods and Applications,* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexDress: The Hiah Level Expression & Protein Purification System* QUIAGEN, Inc., Chatsworth, Calif. Cell culture techniques are described in Doyle, et al. (eds.) (1994) *Cell and Tissue Culture: Laboratory Procedures,* John Wiley and Sons, NY.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Fluorescent labeling of appropriate reagents was performed by standard methods.

Example 1:

Preparation of mAb

The anti-SLAM monoclonal antibody A12 (IgGl) was generated in a fusion of splenocytes from a BALB/c mouse immunized with peripheral blood mononuclear cells activated for 5 hours with 12-0-tetradecanoyl-13 Acetate (TPA) (1 ng/ml) and the $Ca^{2+}$ ionophore A23187 (500 ng/ml) (Calbiochem-Behring Corporation).

Standard procedures were used to screen for appropriate producing clones, and the A12 hybridoma was clonally isolated and subjected to normal analysis, e.g., determination of producing capacity and immunoglobulin type. The A12 hybridoma cell line was deposited with the ATCC on Nov. 10, 1994, and has been assigned ATCC Accession Number HB11760.

Example 2:

Cloning of Human SLAM

COS-7 cells were transfected by electroporation as described in Cocks, et al. (1993) *Int. Immunol.* 5:657–663, with an A10 $CD8^+$ T-cell library DNA prepared as described in McKinney and Parkinson (1987) *J. Immunol. Methods* 96:271–278. Transfected cells were stained with FITC-conjugated anti-SLAM mAb A12 and sorted with a FACStar plus (Becton Dickinson) cell sorting instrument. Plasmid DNA was isolated from sorted cells using a Wizard miniprep kit (Promega Corporation). Plasmid DNA was transformed in Escherichia coli (ElectroMAX, BRL) by electroporation for amplification and then introduced into COS-7 cells. After two rounds of sorting SLAM cDNA clones were enriched to 45% of the total cDNA clones. A 1.8 kb insert in one of these clones (pSURslaml) was sequenced in both strands using the dideoxy chain termination method. This plasmid was deposited with the ATCC on Nov. 10, 1994, and has been assigned ATCC Accession number 69713. Other cDNA clones encoding SLAM variants were isolated and characterized using standard methods. In particular, constructs encoding an extracellular portion of SLAM, or an intracellular portion were prepared by use of appropriate PCR primers and pSURslam1 as template.

Example 3:

Cloning of Mouse SLAM

The mouse SLAM CDNA was cloned from an early thymocyte CDNA library, i.e., $\alpha\beta$, $CD4^-$, $CD8^-$ thymocytes, using DNA representing the extracellular domain of human SLAM as a hybridization probe.

Thymocytes were isolated and stained with primary antibody for 30 min at 4° C., washed twice, and then incubated with FITC-conjugated secondary antibody for 30 min at 4° C. before washing three times. Freshly isolated thymocytes were stained with anti-SLAM monoclonal antibody or IgG, followed by an FITC-conjugated sheep anti-mouse antibody. Cells were assessed for staining using a FACScan (Becton-Dickinson) instrument.

Example 4:

Preparation of Antibodies to Human SLAM

C3H mice were immunized with L-cells stably transfected with pSURslam1. Hybridomas were generated by fusing splenocytes with the NJ1 myeloma line. Detection of the hybridoma cells producing appropriate monoclonal antibodies to human SLAM was by indirect immunofluorescence and flow cytometry. The hybridoma supernatants were screened for reactivity with pSURslam1 transfected L cells, compared to untransfected L cells as control.

Example 5:

Preparation of Antibodies to Mouse SLAM

Rats were immunized with $10^7$ COS cells transfected with pMSLAM1. Hybridomas were prepared by fusing rat popliteal lymph node cells with mouse myeloma cells. Polyclonal serum was also isolated from the rats.

Example 6:

Immunoprecipitation of Human SLAM

Cell-surface proteins of the Th0 T-cell clone B21 were radiolabeled with $^{125}I$-Na (Amersham) using the lactoperoxidose-catalyzed reaction. SLAM was immunoprecipitated using Pansorbin™ (Calbiochem) coated with rabbit anti-mouse Ig and the anti-SLAM anti-serum. The immunoprecipitates were run on a 10% acrylamide minigel (ISS) under reducing conditions, and the dried gel was scanned and analyzed with a Phosphorimager (Molecular Dynamics).

The natural SLAM migrated in a diffuse manner characteristic of glycoproteins, at a mobility characteristic of about 70 kd. If the SLAM was treated overnight with 1.2 μl N-glycanase (Genzyme), the protein migrated at a mobility characteristic of a protein of about 40 kd.

Example 7:

SLAM Expression on Human PBMC

SLAM expression on human PBMC is induced by exposure of the cells to anti-CD3 antibodies for differing time periods. Peripheral blood lymphocytes were incubated with anti-CD3 antibodies (1 μg/ml) for 0, 1, 2, 4, 8, or 24 hours. RNA was extracted and subjected to Northern analysis using SLAM and actin probes, successively. For PCR analysis, appropriate primers were selected for SLAM and for HPRT. 5 ng of CDNA primers was subject to 30 cycles of PCR. The actin signal serves as a normalization factor.

A 4 kb species is apparent at the 2 and 4 hour time points, and is much less detectable at the 0, 1, 8, and 24 hour time points. A 2 kb species is less detectable at the 0 and 1 hour time points, is high at the 2 hour point, decreases at the 4 hour, and stabilizes at the 8 and 24 hour points.

Example 8:

Surface expression of SLAM on mononuclear cells and fetal thymocytes

For FACS analysis, peripheral blood mononuclear cells from a healthy donor were incubated for 6 h with or without TPA and A23187 $Ca^{2+}$ ionophore and stained with anti-CD3 cychrome conjugated (Pharmingen), PE-conjugated A12 mAb, and FITC-labeled CD45RO (Pharmingen). In addition, fetal thymocytes were stained for 30 minutes with PE-conjugated A12 and FITC-conjugated anti-CD3 (Becton Dickinson) and analyzed with a FACScan (Becton Dickinson).

Unstimulated peripheral blood T cells and activated T cells ($CD3^+$ cells) were stained with mAbs to CD45RO and A12. Similarly, fetal thymocytes were stained with anti-CD3 and A12.

The unstimulated T cells had two significant subpopulations: one with little or no SLAM and no CD45RO, this comprising about 49% of the cells; and one with low SLAM and high CD45RO, this subpopulation comprising about 51% of the cells. The CD45RO is a marker for memory T cells, and the SLAM seems to positively correlate with its expression. Naive T cells, which are $CD45RO^-$, also lack SLAM. The SLAM seems to be a useful marker for a memory T cell phenotype.

The activated T cells had two major subpopulations: both with high SLAM, but one had low CD45RO, this making up about 46% of the cells, and the second had high CD45RO. A minor subpopulation, about 4% of the cells, expressed neither CD45RO nor SLAM.

Fetal thymocytes had a pattern which seems to suggest a developmental progression. There is a minor subpopulation of cells, about 2%, which exhibit neither SLAM nor CD3. About 13% of the cells, presumably early development cells, which exhibit low CD3, and high SLAM. About 80% of the cells, presumably at an intermediate stage of development, which express both CD3 and SLAM. A small subpopulation, about 5% of the cells, are mature thymocytes which exhibit low SLAM but high CD3. This probably reflects a progression of SLAM expression with thymocyte maturation. At the earliest maturation stages, SLAM is highly expressed, but eventually disappears.

Example 9:

Cellular Expression of Human SLAM

RNA from various cells and tissues was subject to reverse transcription and PCR using SLAM specific primers. See Table 4 for tissue distribution of human SLAM.

Example 10:

Cellular Expression of Mouse SLAM1

A probe specific for DNA encoding a portion of the extracellular domain of mouse SLAM1 was used to determine tissue distribution of the antigen. A 600 bp probe DNA for murine SLAM was generated by a XhoI/PstI limit digest of the plasmid pMSLAM1 (containing the mouse SLAM CDNA) and purified after gel electrophoresis using a Promega (Madison, Wis.) DNA Clean Up system. All probes were labeled by random priming. The multiple tissue Northern blot was purchased from Clontech and probed using Quick Hyb (Stratagene, La Jolla, Calif.).

The results showed that SLAM was expressed far more abundantly in spleen than in heart, brain, lung, liver, skeletal muscle, kidney, or testes. Testes appeared to have more expression than other tissues but not as much as thymus. Although thymus was not one of the tissues on the Northern blot, SLAM must be expressed there. The mouse SLAM cDNA was cloned from $\alpha\beta$, $CD4^-$, $CD8^-$ thymocytes and, in addition, a monoclonal antibody recognizing mouse SLAM bound specifically to 90% of freshly isolated thymocytes. The frequency of SLAM clones in the thymocyte library was about 1 in 5000.

Example 11:

Species Distribution of SLAM Homologues

DNA was obtained from the various species, digested with EcoRI, electrophoresed, blotted, and transferred, then hybridized with a $^{32}p$ labeled human SLAM probe at 68° C. inclusive of nucleotides 291–901. The blot was washed in 0.2×SSC at 60° C. Southern analysis of genomic DNA from different species indicated that the SLAM gene is well conserved among mammals, e.g., human, monkey, mouse, dog, cow, rabbit, rabbit, but was not detected in chicken or yeast. It was also not detected in rat, but no positive control was provided.

Example 12:

Enhancement of antigen-induced cytokine production by T-cell clones so-stimulated with the anti-SLAM antibody A12

The indicated T cell clones, including the $CD4^+$ T cell clones MoT72 (Th2) and MoT81 (Th0) specific for tetanus toxoid, were cultured in similar conditions as for the proliferative assays, with the following modifications: cultures were performed in 24 well plates culturing $10^6$ T cells with $10^6$ irradiated autologous EBV-transformed B cells, antigen, and mAbs as described for the proliferative assays, in 1 ml Yssel's medium. The supernatants were harvested 24 hours later and the cytokine content was determined by ELISA as described by Chretien, et al. (1989) *J. Immunol. Methods* 117:67–81; or Favre, et al. (1989) *Mol. Immunol.* 26:17–25. The $CD4^+$ T cell clones MOT72 (Th2) and MoT81 (Th0) are specific for tetanus toxoid, and were cultured as described. See Table 5. The mAbs used in this and the costimulation functional studies were purified from ascites by caprilic acid fractionation, see McKinney and Parkinson (1987) *J. Immunol. Methods* 96:271–278, followed by ammonium sulphate precipitation. F(Ab')$_2$ were produced by standard methods digesting the mAbs with pepsin. The control mAbs used were IgG1 from MOPC-21 and IgG1 control mAb (Pharmingen).

TABLE 5

Cytokine production, IFN-γ or pg/ml

| Th type/cell line | no antibody | control Ab | A12 Ab |
|---|---|---|---|
| IFN-γ | | | |
| Th2/NP12 | 962 | 902 | 8303 |
| Th2/NP44 | 1073 | 1319 | 7660 |
| Th2/MoT72 | 496 | 170 | 8585 |
| Th0/ChT38 | 5207 | 7463 | 20569 |
| Tho/MoT81 | 5423 | 6596 | 18176 |
| Th1/HY06 | 5982 | 5904 | 21946 |
| Th1/TA20 | 8374 | 8070 | 15414 |
| IL-4 | | | |
| Th2/NP12 | 6636 | 6486 | 11104 |
| Th2/NP44 | 11617 | 11738 | 10373 |
| Th2/MoT72 | 8805 | 8542 | 16548 |
| Th0/ChT38 | 12907 | 10102 | 15039 |
| Tho/MoT81 | 8455 | 8451 | 11070 |
| Th1/HY06 | 48 | 40 | 90 |
| Th1/TA20 | 62 | 69 | 97 |

Example 13:

Costimulatory Activity for T Cell Activation

Peripheral blood mononuclear cells ($10^5$/well) from recently boosted donors were stimulated with 1 μg/ml of tetanus toxoid or purified protein derivative (PPD) in flat-bottom 96-well plates in 200 μl Yssel's medium in triplicate wells. The cultures were harvested five days later. 1 μCi of $^3$H-TdR was added to each well in the last 16 h of culture, and proliferation was measured by $^3$H-Tdr uptake using a β-counter.

The following CD4$^+$ T cell clones were used: Th0: B21 (Bacchetta, et al. (1990) *J. Immunol.* 144:902–908); MoT72 specific for tetanus toxoid fragment 947–960, and ChT38 specific for tetanus toxoid fragment 16–35 (prepared according to Carballido, et al. (1993) *J. Immunol,* 150:3582–3591. Th1: HY-06 (Haanen, et al. (1991) *J. Exp. Med.* 174:583–592) specific for heat shock protein; TA20 and TA23 specific for purified protein derivative (PPD). Th2: NP12 and NP44 (Th2) specific for the Der-pl (Yssel, et al. (1992) *J. Immunol.* 148:738–745). All T cell clones were harvested 5–7 days following restimulation with PHA and irradiated PBMC as feeder cells and cultured in Yssel's medium (5×10$^4$/well) in the presence or absence of specific antigen (1 μg/ml) or tetanus peptides (100 ng/ml), and 2.5×10$^5$ autologous irradiated (5000 rads) EBV-transformed B cells and mAbs as indicated. Proliferation was measured 3 days later.

Direct induction of T cell clone proliferation by the anti-SLAM mAb A12: The T cell clones B21 and ChT38 were cultured in Yssel's medium in the presence or absence of mAbs and their F(Ab')$_2$. Proliferation was measured 3 days later. Dose dependent proliferation of the two cell lines was observed.

Antigen-specific T-cell proliferation of peripheral blood lymphocytes is enhanced by the anti-SLAM antibody A12: Fab fragments of A12 induced a dose dependent proliferation. PBMC from immunized donors were stimulated with tetanus toxoid or purified protein derivative, with or without mAb fragments.

Co-stimulation of antigen-induced T-cell clone proliferation by A12 antibody: T cell clones NP12, AR142, ChT38, or HY06, were stimulated with their specific antigen with or without mAbs. All results are consistent with an interpretation that either A12, or Fab fragments, can induce proliferation in a dose dependent manner.

Co-stimulation of anti-CD3-induced T-cell clone proliferation by A12 antibody: The T cell clones B21 or TA20 were stimulated with anti-CD3 mAb in the presence or absence of A12 mAb or control IgG1 mAb. In each case, there appeared a dose dependent proliferation with the A12, but not with control antibody. The proliferation was also dependent upon the anti-CD3 amount.

Example 14:

Preparation of SLAM-Ig fusion

In order to identify a potential ligand for the T-cell co-stimulatory molecule SLAM , a recombinant protein (SLAM-Ig) comprising the entire extracellular domain of SLAM fused to the Fc portion of human IgG was generated. SLAM-Ig was made by fusing DNA encoding SLAM to DNA encoding the Fc portion of IgG. DNA encoding the extracellular domain of SLAM was generated by PCR using the plasmid pSURslam1 as template and appropriate primers. After digestion with XhoI the fragment was fused to cDNA encoding the Fc proportion of the IgG1 heavy chain. The SLAM-Ig expression vector was transfected into COS cells and SLAM-Ig affinity purified from the supernatants using protein G-sepharose (Sigma).

Example 15:

SLAM-Ig binds to SLAM expressed on the cell surface

Recombinant SLAM-Ig was effective in neutralizing the SLAM-specific monoclonal antibody A12, indicating that SLAM-Ig had retained a native conformation similar to transmembrane SLAM. Fluorescein conjugated SLAM-Ig was used for fluorocytometric analysis of various cell types and did not bind to many cell types tested. However, SLAM-Ig did bind to cell types which have been shown to express SLAM.

Example 16:

Intramolecular interaction of SLAM-Ig

The T-cell clones B21 (Bacchetta, et al. (1990) *J. Immunol.* 144:902–908) and HY06 (Haanen, et al. (1991) *J. Exp. Med.* 174:583–592) have been described. Thymic epithelial cell lines were generated as described by Galy and Spits (1991) *J. Immunol.* 147:3823–3830, by culture from fetal thymus and the lines TEC, TEC, U937 have been described also by Galy and Spits (1991). L cells carried in RPMI were stably transfected with pSURslam1. Monocytes were purified by negative depletion, and CD32 L cells were provided by Dr. K. Moore (DNAX, Palo Alto). PBMC were freshly isolated from peripheral blood by centrifugation over ficoll (Histopaque-1077, Sigma).

SLAM-Ig did bind to L cells transfected with SLAM (SLAM/L cells), and not to untransfected L cells, indicating that SLAM interacts homophilically. The binding of SLAM-Ig to SLAM transfectants is specific for the SLAM portion of the molecule and not the Ig, as the staining was performed in the presence of excess IgG in the 30% human serum added. Furthermore, SLAM transfectants were not stained by other Fc containing molecules such as CD40-Ig. The binding of SLAM-Ig was about 5-fold lower than the binding to SLAM/L cells observed using an equivalent concentration of the mAb A12. The interaction of SLAM-Ig with cell surface SLAM could be specifically inhibited by an excess of a monoclonal antibody to SLAM. SLAM-Ig binding to transfected cells was not inhibited by EDTA.

The A12 anti-SLAM mAb has been described. Phycoerythrin conjugated CD45RO and CD3 mAbs were purchased from Becton-Dickinson. Cells stained with mAbs, SLAM-Ig or CD40-Ig were washed three times with PBS, 2% FCS and analyzed using a FACScan (Becton-Dickinson).

Fluorescein conjugated SLAM-Ig was used for fluorocytometric analysis of various cell types and did not bind to many cell types tested, including monocytes or thymic epithelial cell lines. However, SLAM-Ig did bind to EBV-transformed B-cell clones and $CD4^+$ T-cell clones, both cell types which we have shown to express SLAM. In no cell types tested did SLAM-Ig bind to cells not expressing SLAM. In addition, the levels of SLAM-Ig binding co-modulated with SLAM expression on $CD45RO^+$ T cells following activation with anti-CD3. The level of SLAM-Ig staining relative to A12 staining on different cell-types was consistent with that observed on L-cell transfectants being 5-fold lower and $Ca^{++}$ independent.

Example 17:

Intermolecular interaction of SLAM-Ig

Gel electrophesis was performed using gels purchased from Integrated Separation Systems and a BioRad multigel apparatus. SDS-electrophoresis was performed under conditions described using a 10% gel and native gel electrophoresis according to manufacturers instructions using a 2–25% gradient gel. Gels were stained with Coomassie Blue. MW standards were purchased from Sigma.

Since a soluble form of SLAM (SLAM-Ig) can interact with cell surface SLAM, it was tested whether SLAM-Ig would interact homophilically, e.g., self recognizing, in solution. Purified SLAM-Ig migrates to a position consistent with its size under SDS-gel electrophoresis and forms one discrete band under reducing or non-reducing conditions. However SLAM-Ig runs anomalously large under native gel electrophoresis, indicative of aggregation of SLAM-Ig molecules in solution. CD40-Ig and other proteins band sharply and according to their size, whereas under the same conditions SLAM-Ig forms a smear beginning at its predicted size of 160,000 without aggregation to over 500,000. Within this range of molecular weights there are two more predominant bands; one at ~160,000 and the other at ~300,000 corresponding to one and two molecules of SLAM-Ig, respectively. Gel filtration of SLAM-Ig confirmed the existence of SLAM-Ig aggregates. Under these conditions, although the monomeric form was more predominant, a peak corresponding to dimeric SLAM was also prominent among the higher molecular weight material.

Example 18:

Homophilic interaction of SLAM leads to T-cell activation

It was also shown that SLAM expressed on activated T cells is a significant co-stimulatory molecule. Engagement of SLAM by the mAb A12 leads to increases in T-cell proliferation and cytokine production. The natural ligand for SLAM should also provide such a co-stimulatory signal. These results suggest that the natural ligand for SLAM is SLAM itself. Thus, the ability of surface SLAM to provide stimulatory signals to T cells was tested. At suboptimal doses of anti-CD3, L cells expressing SLAM provided a direct co-stimulatory signal for T cells to proliferate, whereas, untransfected L cells were ineffective. SLAM/L cells were also capable of directly supporting T-cell proliferation in the absence of anti-CD3 or other stimulatory signals. This ability to directly stimulate T cells in the absence of other stimuli distinguishes SLAM from other co-stimulatory molecules including LFA-3 (Bierer and Hahn (1993) Semin. Immunol. 5:249–261), B7 (Jenkins and Johnson (1993) Curr. Opin. Immunol. 5:361–367), and B70 (Azuma, et al.. (1993) Nature 366:76–79), each of which requires additional signals to induce T cell proliferation.

Since SLAM-SLAM interactions between L cells and T cells have clear functional effects, it was not surprising that L cells transfected with SLAM could be distinguished from untransfected L cells by at least three criteria. First, $SLAM^+$ L cells are resistant to detachment with EDTA requiring over 30 min at 37° C., compared with normal L cells and other L cell transfectants, which become detached within 5 min. Secondly, the SLAM transfectants are strictly contact inhibited whereas, untransfected L cells, although contact inhibited, do continue to proliferate to some extent after confluency has been reached. Thirdly, SLAM transfectants have a more elongated morphology, evident in confluent monolayer cultures where the cells are intertwined, in contrast to normal L cells, which have a more cobblestone appearance. Detached SLAM/L cells did not appear to adhere more readily in suspension.

Example 19:

T cell proliferation induced by SLAM-SLAM interaction is resistant to cyclosporin T cell activation mediated via the TCR is inhibited by cyclosporin. To test whether SLAM-mediated T cell activation was susceptible to cyclosporin, the T cell clone B21 was activated directly with SLAM/L cells in the presence of various concentrations of cyclosporin. SLAM/L cells were capable of directly supporting T-cell proliferation even in the presence of 1 $\mu$g cyclosporin. Interestingly, cyclosporin actually enhanced T cell proliferation induced by homophilic interaction of SLAM at concentrations greater than 100 ng/ml. At 2 $\mu$g/ml, cyclosporin enhanced T cell proliferation induced by SLAM/L cells by 2 fold.

Example 20:

Chromosomal localization

The probe (pSURslaml) was nick-translated with biotin-14 dATP and hybridized in situ at a final concentration of 5 ng/$\mu$l to metaphases from two normal males. The fluorescence in situ hybridization (FISH) method was modified from that described by Callen, et al. (1990). Ann. Genet. 33:219–221, in that chromosomes were stained before analysis with both prodidium iodide (as counter stain) and DAPI (for chromosome identification). Images of metaphase preparations were captured by a CCD camera and computer enhanced.

Twenty metaphases from the first normal male were examined for fluorescent signal. Nineteen of these metaphases showed signal on one or both chromatids of chromosome 1 in the region lq21.2–lq23; 34% of this signal was at lq21.3 and 59% was at lq22. This indicated a probable location close to the interface of these two bands. There was a total of 4 non-specific background dots observed in these 20 metaphases. A similar result was obtained for hybridization of the probe to 20 metaphases from the second normal male.

The gene maps to the same region as one which correlates with systemic lupus erythematosis susceptibility. The two genes may be the same, e.g., SLAM reagents may be useful either as a direct therapeutic for the condition, or the gene may be a useful genetic marker for mapping such gene.

Example 21:

Kd of SLAM-SLAM interaction

The equilibrium constants for SLAM/SLAM interactions were analyze by surface plasmon resonance using a BIAcore™ (Pharmacia) instrument. An anti-SLAM Ab 7D4 was used.

Ab 7D4/SLAM-Ig and SLAM-Ig/SLAM-Ig binding kinetics and affinity were measured. About 8000 resonance units (RUs) of SLAM-Ig were covalently attached to the dextran matrix in the sensor chip via its lysines, according to the manufacturer's protocol (BIAcore™ manual, Pharmacia Biosensor). Buffer (phosphate-buffer saline, PBS, pH 7.0) was passed through the flow cell until all of the dissociable protein was removed and the baseline remained stable. Solutions containing various concentrations of the antibody 7D4 in PBS (ranging from 10 nM to 500 nM) were then passed through the flow cell. An increase in mass of protein bound was observed, followed by a decrease when the protein solution was replaced with buffer. A non-linear data analysis protocol, O'Shannessy, et al. (1993) *Anal. Biochem.* 212:457–468, was used to analyse the data to determine the association ($k_a$) and dissociation ($k_d$) rate constants. See Table 6. The equilibrium dissociation constant $K_d$ was then calculated from the ratio $k_d/k_a$.

SLAM-Ig/SLAM-Ig binding kinetics were measured in a similar manner. After immobilization of SLAM-Ig to the chip, solutions of SLAM-Ig at concentrations ranging from 100 nM to 1500 nM were passed through the flow cell at a flow rate of 5 μl/min. From the association and dissociation phases, the corresponding rate constants and thus the equilibrium binding constant were obtained.

Both the $k_{on}$ and $k_{off}$ rates are slower than other cell-cell adhesion interactions. The $K_d$ is some 10–100 times higher than other cell-cell adhesion interactions, e.g., CD2 interaction with CD48 (about 60–80 μm).

TABLE 6

Association and dissociation rate constants[1] and the apparent equilibrium constant $K_d$ for SLAM/SLAM and SLAM/Ab 7D4 interactions

| Immobilized surface | Ligand | $k_{on}$ ($\times 10^4 M^{-1} s^{-1}$) | $k_{off}$ ($s^{-1}$) | $K_d$ |
|---|---|---|---|---|
| SLAM-Ig | Ab 7D4 | 1.32 | $5.5 \times 10^{-5}$ | 4.2 nM |
| SLAM-Ig | SLAM-Ig | 1.2 | 0.011 | 0.92 mM |

[1]The standard errors in the parameters were estimated to be: $k_{on}$, 20%; $k_{off}$, 10%; $k_d$, 24%.

What is claimed is:

1. A substantially pure or recombinant SLAM protein:
   a) consisting of SEQ ID NO: 2,4, 6, 8, 10, or 12;
   b) encoded by a polynucleotide comprising the open reading frame of SEQ ID NO: 1,3,5,7,9,or 11; or
   c) encoded by a naturally occurring allelic variant of a polynucleotide comprising the open reading frame of SEQ ID NO: 1, 3, 5, 7, 9, or 11.

2. The recombinant protein of claim 1, encoded by a naturally occurring allelic variant of a polynucleotide comprising the open reading frame of SEQ ID NO: 1,3,5, or 7.

3. A substantially pure or recombinant SLAM protein which:
   a) has an apparent molecular weight 70 kD for naturally glycosylated SLAM protein, as determined by SDS/polyacrylamide gel electrophoresis; and
   b) is found on immature $CD3^{low}CD4^+CD8^+$ fetal thymocytes or peripheral blood $CD45RO^{high}$ memory T cells;
   wherein said SLAM protein has at least one of the following properties:
   i) is rapidly induced on naive $CD45RA^+$ cells following activation;
   ii) is a self-ligand; or
   iii) stimulates proliferation of $CD4^+$ T cell dones upon specific engagement with said SLAM polypeptide.

4. A substantially pure or recombinant polypeptide comprising at least 12 contiguous amino acid residues identical to at least 12 contiguous amino acid residues of said SLAM protein of claim 1.

5. A substantially pure or recombinant polypeptide comprising at least 16 contiguous amino acid residues identical to at least 16 contiguous amino acid residues of said SLAM protein of claim 2.

6. A substantially pure or recombinant polypeptide comprising at least 20 contiguous amino acid residues identical to at least 20 contiguous amino acid residues of said SLAM protein of claim 1.

7. A substantially pure or recombinant polypeptide comprising at least 30 contiguous amino acid residues that are identical to at least 30 contiguous amino acid residues of said SLAM protein of claim 1.

8. A substantially pure or recombinant polypeptide comprising the intracellular domain, the extracellular domain, or the mature form of said SLAM protein of claim 1.

9. A substantially pure or recombinant polypeptide comprising the intracellular domain, the extracellular domain, or the mature form of said SLAM protein of claim 3.

10. A substantially pure or recombinant polypeptide comprising an immunogenic peptide of said SLAM protein of claim 1.

11. A substantially pure or recombinant polypeptide comprising an immunogenic peptide of said SLAM protein of claim 3.

12. A substantially pure or recombinant polypeptide comprising an immunogenic peptide of said polypeptide of claim 4.

13. A substantially pure or recombinant pplypeptide comprising an immunogenic peptide of said polypeptide of claim 7.

14. A fusion protein comprising said polypeptide of claim 4 and:
   a) a detection or purification tag selected from the group consisting of a FLAG, His6, and immunoglobulin peptide;
   b) a carrier protein selected from the group consisting of keyhole limpet hemocyanin, bovine serum albumin, and tetanus toxoid; or
   c) another peptide selected from the group consisting of luciferase, bacterial β-galactosidase, trpE, protein A, β-lactamase, alpha amylase, alcohol dehydrogenase, and yeast alpha mating factor.

15. A fusion protein comprising said polypeptide of claim 7 and:
   a) a detection or purification tag selected from the group consisting of a FLAG, His6, and immunoglobulin peptide;

b) a carrier protein selected from the group consisting of keyhole limpet hemocyanin, bovine serum albumin, and tetanus toxoid; or c) another peptide selected from the group consisting of luciferase, bacterial β-galactosidase, trpE, protein A, β-lactamase, alpha amylase, alcohol dehydrogenase, and yeast alpha mating factor.

16. A fusion protein comprising said polypeptide of claim 11 and:

a) a detection or purification tag selected from the group consisting of a FLAG, His6, and immunoglobulin peptide;

b) a carrier protein selected from the group consisting of keyhole limpet hemocyanin, bovine serum albumin, the tetanus toxoid; or c) another peptide selected from the group consisting of luciferase, bacterial β-galactosidase, trpE, protein A, β-lactamase, alpha amylase, alcohol dehydrogenase, and yeast alpha mating factor.

17. A composition comprising said polypeptide of claim 4, that is:

a) in a pharmaceutically acceptable carrier;

b) in a sterile composition;

c) in a buffered solution; or d) in an aqueous suspension.

18. The composition of claim 17, in water, saline, buffer, or an aqueous solution.

19. A composition comprising said polypeptide of claim 7, that is:

a) in a pharmaceutically acceptable carrier;

b) in a sterile composition;

c) in a buffered solution; or d) in an aqueous suspension.

20. A composition comprising said polypeptide of claim 11, that is:

a) in a pharmaceutically acceptable carrier;

b) in a sterile composition;

c) in a buffered solution; or d) in an aqueous suspension.

21. A polypeptide of claim 4, that is:

a) denatured;

b) immunopurified;

c) attached to a solid substrate;

d) detectably labeled; or e) chemically synthesized.

22. A polypeptide of claim 11, that is:

a) denatured;

b) immunopurified;

c) attached to a solid substrate;

d) detectably labeled; or e) chemically synthesized.

23. A kit comprising said protein of claim 1, and:

a) a compartment comprising said protein; or b) instructions for use or disposal of reagents in said kit.

24. A kit comprising said polypeptide of claim 3, and:

a) a compartment comprising said protein; or b) instructions for use or disposal of reagents in said kit.

25. A kit comprising said polypeptide of claim 4, and:

a) a compartment comprising said polypeptide; or b) instructions for use or disposal of reagents in said kit.

26. A kit comprising said polypeptide of claim 7, and:

a) a compartment comprising said polypeptide; or b) instructions for use or disposal of reagents in said kit.

27. A kit comprising said polypeptide of claim 11, and:

a) a compartment comprising said polypeptide; or b) instructions for use or disposal of reagents in said kit.

28. The SLAM protein of claim 1, which:

a) induces cytokine production by $CD4^+$ T cell clones;

b) reverses a phenotype of a Th2 cell clone to a Th0 T cell done; or c) has an apparent molecular weight of about 40 kD as determined by SDS polyacrylamide gel electrophoresis, following N-glycanase treatment of said SLAM protein.

29. The SLAM protein of claim 3, which:

a) induces cytokine production by $CD4^+$ T cell clones;

b) reverses a phenotype of a Th2 cell clone to a Th0 T cell clone; or c) has an apparent molecular weight of about 40 kD as determined by SDS polyacrylamide gel electrophoresis, following N-glycanase treatment of said SLAM protein.

30. The polypeptide of claim 9, wherein:

a) said intracellular domain is from amino acid residue 28 to 230 of SEQ ID NO: 2; or b) said extracellular domain is from amino acid residue 258 to 335 of SEQ ID NO: 2.

* * * * *